US009079983B2

(12) United States Patent
Carlson et al.

(10) Patent No.: US 9,079,983 B2
(45) Date of Patent: Jul. 14, 2015

(54) CHEMOSELECTIVE ENRICHMENT FOR COMPOUND ISOLATION

(75) Inventors: Erin E. Carlson, Bloomington, IN (US); Darci Trader, Bloomington, IN (US); Antoinette Odendaal, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 315 days.

(21) Appl. No.: 13/571,591

(22) Filed: Aug. 10, 2012

(65) Prior Publication Data

US 2013/0041106 A1   Feb. 14, 2013

Related U.S. Application Data

(60) Provisional application No. 61/521,839, filed on Aug. 10, 2011, provisional application No. 61/543,972, filed on Oct. 6, 2011.

(51) Int. Cl.

| *C08F 8/00* | (2006.01) |
|---|---|
| *C08F 8/10* | (2006.01) |
| *C08F 12/14* | (2006.01) |
| *C07C 269/08* | (2006.01) |
| *C07C 303/44* | (2006.01) |
| *C07C 213/10* | (2006.01) |
| *C07C 319/28* | (2006.01) |
| *C07D 451/10* | (2006.01) |
| *C07C 231/24* | (2006.01) |
| *C07D 207/12* | (2006.01) |
| *C07C 249/14* | (2006.01) |
| *C07D 207/34* | (2006.01) |
| *C07D 209/18* | (2006.01) |
| *C07C 253/34* | (2006.01) |
| *C07D 211/40* | (2006.01) |
| *C07D 211/62* | (2006.01) |
| *B01D 15/08* | (2006.01) |
| *B01J 20/32* | (2006.01) |
| *C07J 1/00* | (2006.01) |
| *C07J 5/00* | (2006.01) |
| *C07J 9/00* | (2006.01) |
| *C07J 51/00* | (2006.01) |

(52) U.S. Cl.
CPC . *C08F 8/10* (2013.01); *B01D 15/08* (2013.01); *B01J 20/321* (2013.01); *B01J 20/3261* (2013.01); *C07C 213/10* (2013.01); *C07C 231/24* (2013.01); *C07C 249/14* (2013.01); *C07C 253/34* (2013.01); *C07C 269/08* (2013.01); *C07C 303/44* (2013.01); *C07C 319/28* (2013.01); *C07D 207/12* (2013.01); *C07D 207/34* (2013.01); *C07D 209/18* (2013.01); *C07D 211/40* (2013.01); *C07D 211/62* (2013.01); *C07D 451/10* (2013.01); *C07J 1/0011* (2013.01); *C07J 5/0053* (2013.01); *C07J 9/005* (2013.01); *C07J 51/00* (2013.01); *C08F 8/00* (2013.01); *C08F 12/14* (2013.01); *C07C 2101/14* (2013.01); *C07C 2102/08* (2013.01); *C07C 2102/30* (2013.01); *C07C 2103/26* (2013.01)

(58) Field of Classification Search
CPC ............... C07J 5/00; C07J 9/00; C08F 12/14; C08F 8/10; C08F 8/00; C08F 8/42; C08F 12/18; C08F 8/12; B01J 20/3261; B01J 20/321; B01J 20/281; B01D 15/08; C07D 211/04; C07D 209/18; C07D 211/62; C07D 207/34; C07D 207/12; C07D 451/10; C07C 249/14; C07C 231/24; C07C 319/28; C07C 303/44; C07C 271/16; C07C 271/24; C07C 215/12; C07C 215/16; C07C 215/76; C07C 233/25; C07C 271/22; C07C 323/59; C07C 251/60; C07C 255/57; C07C 233/51; C07C 311/16; C07C 2103/26; C07C 2102/08; C07C 213/10; C07C 269/08; C07C 2102/30; C07C 2101/14
USPC ............. 525/106, 100, 55, 50, 165, 232, 191, 525/317, 242, 193, 192, 199, 70, 63, 88; 520/1; 528/480, 491, 482
See application file for complete search history.

(56) References Cited

U.S. PATENT DOCUMENTS 4,721,800 A * 1/1988 Chapman et al. ............. 556/405

OTHER PUBLICATIONS

Newman, David J., and Gordon M. Cragg. "Natural Products as Sources of New Drugs over the Last 25 Years." Journal of natural products 70.3 (2007): 461-477.
Carlson, Erin E. "Natural products as chemical probes." ACS chemical biology 5.7 (2010): 639-653.
Böttcher, Thomas, Maximilian Pitscheider, and Stephan A. Sieber. "Natural products and their biological targets: proteomic and metabolomic labeling strategies." Angewandte Chemie International Edition 49.15 (2010): 2680-2698.
Månsson, Maria, et al. "Explorative solid-phase extraction (E-SPE) for accelerated microbial natural product discovery, dereplication, and purification." Journal of Natural Products 73.6 (2010): 1126-1132.
Araya, Juan J., et al. "Application of phase-trafficking methods to natural products research." Journal of natural products 73.9 (2010): 1568-1572.

(Continued)

*Primary Examiner* — Ling Choi
*Assistant Examiner* — Jessica E Whiteley
(74) *Attorney, Agent, or Firm* — Barnes & Thornburg LLP

(57) ABSTRACT

Chemoselective isolation of hydroxyl group-containing and carboxyl group-containing compounds is accomplished via formation of polymeric silyl ethers and polymeric siloxyl esters, respectively. Preparation of chemoselective polymeric reagents for capture of hydroxyl group containing compounds and carboxyl group containing compounds is described.

2 Claims, No Drawings

(56) References Cited

OTHER PUBLICATIONS

Watve, Milind G., et al. "How many antibiotics are produced by the genus *Streptomyces*?." Archives of microbiology 176.5 (2001): 386-390.

Carlson, Erin E., and Benjamin F. Cravatt. "Chemoselective probes for metabolite enrichment and profiling." Nature methods 4.5 (2007): 429-435.

Carlson, Erin E., and Benjamin F Cravatt. "Enrichment tags for enhanced-resolution profiling of the polar metabolome." Journal of the American Chemical Society 129.51 (2007): 15780-15782.

Odendaal, Antoinette Y., Darci J. Trader, and Erin E. Carlson. "Chemoselective enrichment for natural products discovery." Chemical Science 2.4 (2011): 760-764.

Henkel, Thomas, et al. "Statistical investigation into the structural complementarity of natural products and synthetic compounds." Angewandte Chemie International Edition 38.5 (1999): 643-647.

Bringmann, G.; Reichert, Y.; Kane, V. V. *Tetrahedron* 2004, 60, 3539.

Meloni, Marco M., et al. "Synthesis and applications of <i>tert</i>-alkoxysiloxane linkers in solid-phase chemistry." Tetrahedron 63.2 (2007): 299-311.

Weinberg, Jennifer M., Stephen P. Gitto, and Karen L. Wooley. "Synthesis and Characterization of Degradable Poly (silyl ester) s." Macromolecules 31.1 (1998): 15-21.

Wang, Min, Jennifer M. Weinberg, and Karen L. Wooley. "Synthesis, Characterization and Degradation of Poly (silyl ester) s." Macromolecules 31.22 (1998): 7606-7612.

Ojima, Yuko, Kazuya Yamaguchi, and Noritaka Mizuno. "An Efficient Solvent-Free Route to Silyl Esters and Silyl Ethers." Advanced Synthesis & Catalysis 351.9 (2009): 1405-1411.

Liang, Huan, Lin Hu, and E. J. Corey. "Di-tert-butylisobutylsilyl, Another Useful Protecting Group." Organic Letters 13.15 (2011): 4120-4123.

Huczynski, A.; Stefanska, J.; Przybylski, P.; Brzezinski, B.; Bartl, F., Bioorg. Med. Chem. Lett. 2008, 18, 2585.

Wallace, K. K.; Payne, G. F.; Speedie, M. K. *J. Ind. Microbiol. Biotechnol.* 1990, 6, 43.

Mbah, Godfrey C., and John L. Speier. "Equilibria between Me<sub>x</sub>SiCl<sub>4-x</sub>, <i>x</i>= 3, 2, 1, 0 and alkyl carboxylate esters." Journal of organometallic chemistry 271.1 (1984): 77-82.

Chauhan, Moni, Bhanu PS Chauhan, and Philip Boudjouk. "An efficient Pd-catalyzed route to silyl esters." Organic letters 2.8 (2000): 1027-1029.

Huang, Xiaogen, et al. "Silyl methallylsulfinates: efficient and powerful agents for the chemoselective silylation of alcohols, polyols, phenols and carboxylic acids." Chemical communications 10 (2005): 1297-1299.

Clardy, Jon, and Christopher Walsh. "Lessons from natural molecules." Nature 432.7019 (2004): 829-837.

Newman, D. J.; Cragg, G. M. *J. Nat. Prod.* 2012, 75, 311.

Koehn, Frank E., and Guy T. Carter. "The Evolving Role of Natural Products in Drug Discovery." Nature Reviews Drug Discovery 4.3 (2005): 206-220.

Butler, Mark S. "The role of natural product chemistry in drug discovery." Journal of Natural Products 67.12 (2004): 2141-2153.

Sticher, Otto. "Natural product isolation." Natural product reports 25.3 (2008): 517-554.

Gualtieri, Maxime, et al. "The Antibiotics in the Chemical Space." Current Medicinal Chemistry 16.3 (2009): 390-393.

Hu, Yonghan, et al. "Novel polymer-supported bialkylsilanes and their use in solid-phase organic synthesis." The Journal of Organic Chemistry 63.13 (1998): 4518-4521.

DiBlasi, Christine M., Daniel E. Macks, and Derek S. Tan. "An acid-stable tert-butyldiarylsilyl (TBDAS) linker for solid-phase organic synthesis." Organic letters 7.9 (2005): 1777-1780.

Cheminat, Annie, et al. "Removal of allergens from natural oils by selective binding to polymer supports. II. Application of aminated resins to isoalantolactone and costus oil." *Canadian Journal of Chemistry* 59.10 (1981): 1405-1414.

Boehm, Terri L., and HD Hollis Showalter. "Development of a Novel Silyl Ether Linker for Solid-Phase Organic Synthesis1." The Journal of organic chemistry 61.19 (1996): 6498-6499.

B. A. Sobin and J. Tanner, F. W., J. Am. Chem. Soc., 1954, 76, 4053.

J. M. J. Frechet, A. J. Hagen, C. Benezra, & A. Cheminat, "Polymeric Separation Media: Binding of 2,.beta.-Unsaturated Carbonyl Compounds to Insoluble Resins through Michael Additions or Chelation of Derivatives," Pure & Appl. Chem., vol. 54, No. 11 (1982), pp. 2181-2188.

A. P. Grollman, J. Biol. Chem., 1967, 242, 3226-3233.

Berdy, J. *J. Antibiot.* 2005, 58, 1.

Grabowski, Kristina, Karl-Heinz Baringhaus, and Gisbert Schneider. "Scaffold diversity of natural products: inspiration for combinatorial library design." Natural product reports 25.5 (2008): 892-904.

Tallarico, John A., et al. "An alkylsilyl-tethered, high-capacity solid support amenable to diversity-oriented synthesis for one-bead, one-stock solution chemical genetics." Journal of combinatorial chemistry 3.3 (2001): 312-318.

Trader, D. J.; Carlson, E. E. *Org. Lett.* 2011, 13, 5652.

Trader, D. J.; Carlson, E. E. *Mol. Biosyst.* 2012, 8, 2484.

Rishton, G. M. *Am J Cardiol* 2008, 101, 43.

Dimitrios, B. *Trends Food Sci. Technol.* 2006, 17, 505.

Crouch, R. D. *Tetrahedron* 2004, 60, 5833.

Crouch, R. D. *Tetrahedron* 2013, 69, 2383.

Crouch, R. D.; Stieff, M.; Frie, J. L.; Cadwallader, A. B.; Bevis, D. C. Tetrahedron Lett. 1999, 40, 3133.

Wang, H.; Yeo, S. L.; Xu, J.; Xu, X.; He, H.; Ronca, F.; Ting, A. E.; Wang, Y.; Yu, V. C.; Sim, M. M. *J. Nat. Prod.* 2002, 65, 721.

Wilson, N. S.; Keay, B. A. *Tetrahedron Lett.* 1997, 38, 187.

Yan, L.; Zhao, F.; Gan, Y.; Zhao, J.; Jiang, Z. *Syn. Comm.* 2012, 42, 285.

Wang, B.; Sun, H.-X.; Sun, Z.-H. *J. Org. Chem.* 2009, 74, 1781.

Yeom, C.-E.; Kim, H. W.; Lee, S. Y.; Kim, B. M. *Synlett* 2007, 1, 146.

Collington, E. W.; Finch, H.; Smit, I. J. *Tetrahedron Lett.* 1985, 26, 681.

Frie, J. L.; Jeffrey, C. S.; Sorenson, E. J. *Org. Lett.* 2009, 11, 5394.

Karavalakis, G.; Anastopoulos, G.; Stournas, S. *Appl. Energ.* 2011, 88, 3645.

Simoni, D.; Invidiata, F. P.; Manferdini, M.; Lampronti, I.; Rondanin, R.; Roberti, M.; Pollini, G. P. *Tetrahedron Lett.* 1998, 39, 7615.

Zhu, A.; Jiang, T.; Wang, D.; Han, B.; Liu, L.; Huang, J.; Zhang, J.; Sun, D. *Green Chem.* 2005, 7, 514.

Oyama, K.; Kondo, T. *Org. Lett.* 2003, 5, 209.

Kovacevic, B.; Z.B., M. *Org. Lett.* 2001, 3, 1523.

Charest, M. G.; Siegel, D. R.; Myers, A. G. *J. Am. Chem. Soc.* 2005, 127, 8292.

Evans, D. A.; Dinsmore, C. J.; Ratz, A. M.; Evrard, D. A.; Barrow, J. C. *J. Am. Chem. Soc.* 1997, 119, 3417.

Yu, X. M.; Shen, G.; Necker, L.; Blake, H.; Holzbeierlein, J.; Cronk, B.; Blagg, B. S. J. *J. Am. Chem. Soc.* 2005, 127, 12778.

\* cited by examiner

CHEMOSELECTIVE ENRICHMENT FOR COMPOUND ISOLATION

CROSS-REFERENCE TO RELATED APPLICATIONS

This application claims the benefit of U.S. Provisional Application No. 61/521,839, filed Aug. 10, 2011, and U.S. Provisional Patent Application No. 61/543,972, filed Oct. 6, 2011 under 35 U.S.C. §119(e), the disclosures of each of which are incorporated by reference herein in their entireties.

GOVERNMENT RIGHTS

This invention was made with government support under GM082983 awarded by the National Institutes of Health. The Government has certain rights in the invention.

TECHNICAL FIELD

This invention pertains to chemoselective isolation of hydroxyl group containing compounds and/or compounds containing carboxylic acid groups using polymeric reagents.

PART A

Background and Summary

The search for molecules possessing the features required to modulate biological processes is a longstanding scientific goal. Natural products have been a continual source of inspiration, yielding many therapeutic agents and targets for (bio) synthetic studies. Natural products and their derivatives account for nearly half of the drugs currently on the market [1a] and have been used extensively as chemical probes. [2a] Despite recent advances, [3a] the isolation of novel natural products remains challenging as the use of traditional isolation methods often results in rediscovery of known compounds and/or the loss of bioactivity. [4a]

Current purification methods, such as high performance liquid chromatography (HPLC) or size exclusion chromatography, separate molecules by their physiochemical properties including polarity, charge, and size. New technologies are needed that isolate molecules based upon alternative characteristics then those presently used for natural product discovery, which are biased towards abundant molecules. The development of chemoselective isolation strategies to facilitate enrichment of subclasses of biological molecules including metabolites [5a] and alcohol-containing natural products has been described. [6a] For natural products discovery, a controllably reversible reaction is used to immobilize the compounds in a mixture that includes the targeted functional group class onto solid support. Following an extensive wash protocol, the enriched subpool is tracelessly released to enable characterization of the natural products present.

Generation of a chemoselective isolation reagent toolkit is significant because it provides a means for discovery of natural products that are unlikely to be identified by traditional strategies due to low isolation yields, poor compound resolution, and/or the presence of interfering compounds. Furthermore, a functional group targeted method can offer insight into the structural content of compounds prior to characterization efforts.

DETAILED DESCRIPTION

A reversible enrichment tag for the hydroxyl functional group, which was targeted by formation of a silyl ether bond using a chlorodiethylsiloxane polystyrene resin has been described. [6a] The isolated compound pool was readily released from the resin by treatment with a fluoride source. Described herein is a strategy for chemoselective isolation of compounds that include a carboxylic acid functional group. This moiety is present in approximately 15% of natural products and 25% of drugs, [7a] making it an important group to target with the reversible enrichment method described herein. Use of an anion exchange resin to separate a subpool of natural products, including carboxylic acids has been described. [3ba] However, other acidic groups, such as phenols, [7a] were readily isolated using the reported strategy. Additionally, the non-covalent interaction that this method is dependent upon is not strong enough to tolerate extensive washing protocols resulting in substantial carryover between fractions. Clearly, development of a covalent and chemoselective enrichment strategy is warranted.

Herein described is a silicon-functionalized resin architecture (3) that displays significant preference for reaction with carboxylic acid-containing molecules. This resin utilizes a diisopropylsiloxane capture moiety, which forms a siloxyl ester bond with carboxylic acids (4; Scheme 1). [9a] Following capture, the enriched compounds are readily released from resin using a fluoride source. This result is surprising given the well known instability of silyl esters. [10a] Carboxylic acids were enriched using resin 3 with yields of ~90% (Table S1). This resin also promoted isolation of alcohol-containing compounds (yields 6-18%). Amine- and thiol-containing compounds were not captured to an appreciable extent by this resin (0-3%; Table S1).

TABLE S1

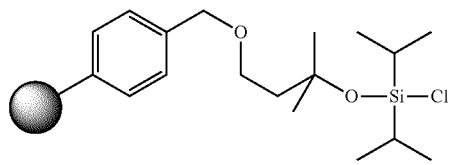 [SMILES: Cc1ccc(COCCC(C)(C)O[Si](Cl)(C(C)C)C(C)C)cc1]

3

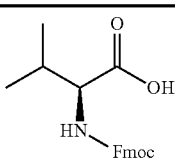

S4          85%

TABLE S1-continued

| Structure | # | Yield |
|---|---|---|
| indol-3-yl acetic acid | S5 | 98% |
| HO-(CH2)3-NHFmoc | 17 | 18% |
| 2-(N-ethyl-N-phenylamino)ethanol | S6 | 6% |
| 3-(dimethylamino)phenol | 18 | 10% |
| tryptamine | S7 | 0% |
| Cbz-Lys-OMe | 19 | 0% |
| N-Boc-cysteine methyl ester | 20 | 3% |
| resin-linked silyl chloride linker | S1 | |
| Fmoc-Val-OH | S4 | 10% |

TABLE S1-continued

| Structure | # | Yield |
|---|---|---|
| indol-3-yl-acetic acid | S5 | 22% |
| HO-(CH2)3-NHFmoc | 17 | 52% |
| 2-(N-ethyl-N-phenylamino)ethanol | S6 | 90% |
| 3-(dimethylamino)phenol | 18 | 52% |
| tryptamine | S7 | 2% |
| Nε-Cbz-L-lysine methyl ester | 19 | 0% |
| N-Boc-L-cysteine methyl ester | 20 | 11% |

| Structure | # |
|---|---|
| polymer-supported chlorodiethylsilyl linker | S2 |

| Structure | # | Yield |
|---|---|---|
| Fmoc-L-Val-OH | S4 | 31% |

TABLE S1-continued

| Structure | # | Yield |
|---|---|---|
| indol-3-yl-acetic acid | S5 | 25% |
| HO-CH2CH2CH2-NHFmoc | 17 | 58% |
| N-ethyl-N-phenyl ethanolamine (HO-CH2CH2-N(Et)(Ph)) | S6 | 74% |
| 3-(dimethylamino)phenol | 18 | 41% |
| tryptamine | S7 | 4% |
| Cbz-Lys-OMe | 19 | 0% |
| Boc-Cys-OMe | 20 | 0% |
| polymer-bound aryl-propyl-diisopropylsilyl triflate | S3 | |
| Fmoc-Val-OH | S4 | 38% |

TABLE S1-continued

| Structure | # | Yield |
|---|---|---|
| Indole-3-acetic acid | S5 | 96% |
| HO~~~NHFmoc | 17 | 63% |
| N,N-(ethyl)(2-hydroxyethyl)aniline | S6 | 70% |
| 3-(dimethylamino)phenol | 18 | 53% |
| Tryptamine | S7 | 3% |
| Cbz-Lys-OMe | 19 | 45% |
| N-Boc-Cys-OMe | 20 | 46% |

Table S1: Comparison of the capture abilities of several dialkyl siloxyl chloride resins and a diisopropylsilyl triflate resin. Each value is an average of four replicates.

The chemical characteristics resulting in formation of a stable siloxyl ester species and affording selectivity towards carboxylic acids are described herein. A series of resin derivatives was synthesized and assessed for their ability to capture a standard set of compounds. The steric environment about the silicon atom contributes to ester stability. Resin 3 includes relatively hindered isopropyl groups. Use of several resin variants with altered steric properties are described herein. The dimethyl- and diethyl-substituted resins, S1 and S2, respectively, favored enrichment of alcohol-containing compounds with yields of ~70% and exhibited lower yields of carboxylic acids (~20%; Table S1). These data suggest that the nature of the alkyl substituents on the silicon atom is critical to preferential functional group capture.

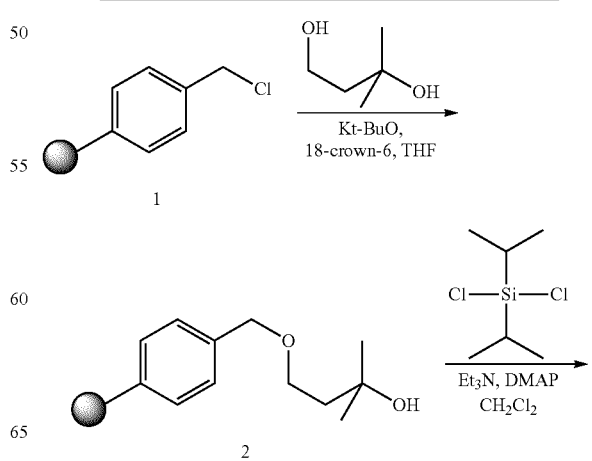

Scheme 1. Synthesis of the diisopropyl siloxyl chloride resin.

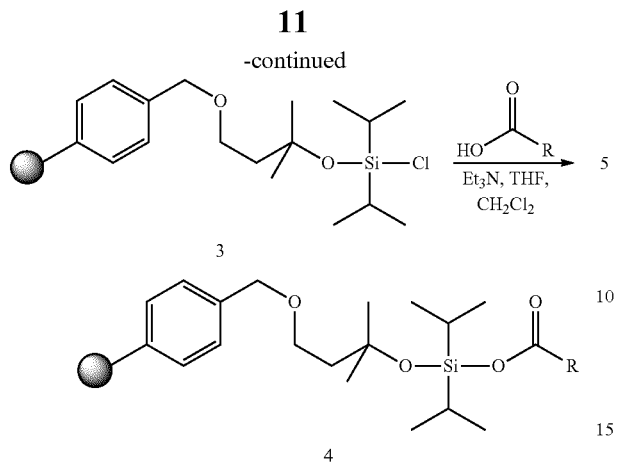

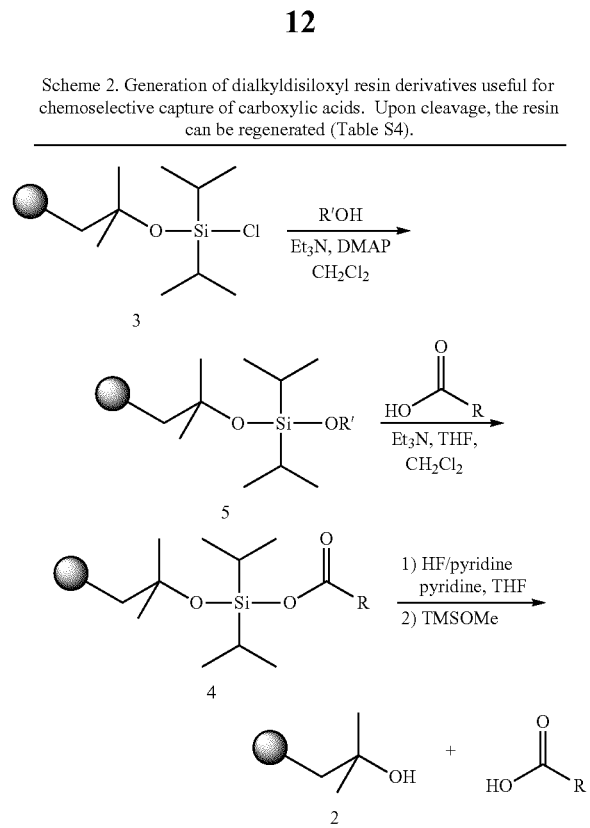

Scheme 2. Generation of dialkyldisiloxyl resin derivatives useful for chemoselective capture of carboxylic acids. Upon cleavage, the resin can be regenerated (Table S4).

These results appear to be consistent with what is known about silyl and siloxyl ester stability, i.e. bulkier silyl and siloxy esters are more stable. [10a] Silylating reagents are generally not chemoselective for carboxylic acids often forming more stable bonds with the hydroxyl group. [11a] A bulky reagent, di-tert-butylisobutylsilyl triflate, has been described that selectively protects carboxylic acids over alcohols in some substrates. [12a] This protecting group also readily forms stable conjugates with amines. As described above, the presence of the diisopropyl substituents on the silicon was not enough to afford a selective reagent. Without being bound by theory, it is believed that the oxygen linker between the resin and the silicon atom is also important for selectivity as a diisopropylsilyl-functionalized resin facilitated the isolation of alcohols, carboxylic acids, thiols and amines (S3, Table S1 and Ref 6a). As described herein, selective capture of carboxylic acids is accomplished with the diisopropyl siloxyl scaffold.

Efforts to achieve the desired chemoselectivity by preferentially cleaving either the alcohols or acids captured by resin 3 were unsuccessful. It was discovered, as described herein, that modification of the leaving group enables selective capture of the more nucleophilic carboxylate. Accordingly, a series of dialkyldisiloxane resins was generated by alcoholysis of the silyl chloride (5, Scheme 2).

Described herein are the loading capacities and enrichment yields provided by three illustrative resins, methoxy- (6), isopropoxy- (7), and t-butoxy-substituted (8), with an illustrative set of carboxylic acids (Tables 1, S2, and S3). A good combination of loading capacity and breadth of carboxylic acid capture was obtained with the isopropoxy derivative (7). The t-butoxy derivative (8) was effective for capture of less hindered substrates but it was not effective for the efficient enrichment of sterically encumbered compounds. The methoxy derivative (6) showed moderate to low yields. Without being bound by theory, it is believed that the low yields obtained with 6 results from its relatively poor leaving group potential. Each of these three derivatives displayed complete carboxylic acid chemoselectivity (Table 1).

TABLE 1

Enrichment yields of model carboxylic acid-, alcohol-, amine- and thiol-containing molecules with dialkyldisiloxane resin derivatives.

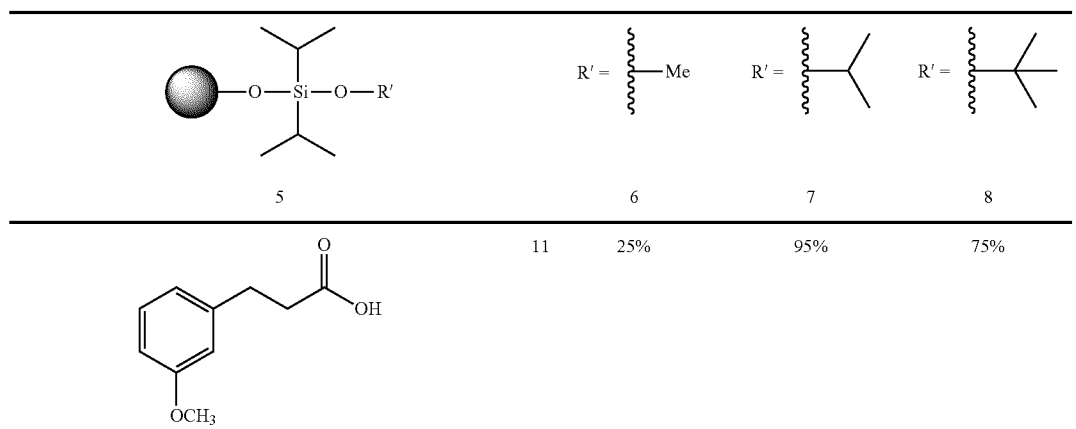

| 5 | 6 | 7 | 8 |
|---|---|---|---|
| 11 | 25% | 95% | 75% |

TABLE 1-continued
Enrichment yields of model carboxylic acid-, alcohol-, amine- and thiol-containing molecules with dialkyldisiloxane resin derivatives.
| | | | | |
|---|---|---|---|---|
| 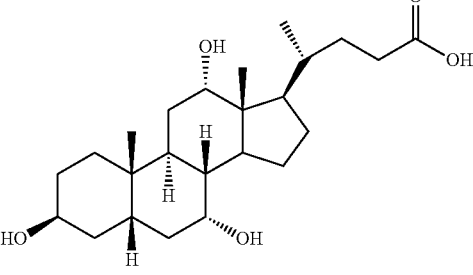 | 12 | 73% | 94% | 53% |
| 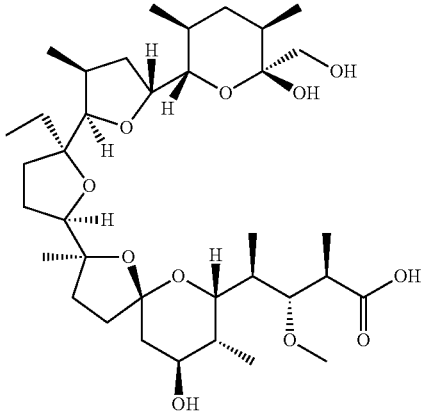 [SMILES: CC[C@@]1([C@@H]2O[C@@H]([C@H]3O[C@@](O)(CO)[C@H](C)C[C@@H]3C)C[C@@H]2C)CC[C@H]([C@]2(C)CC[C@]3(C[C@H](O)[C@@H](C)[C@@H]([C@@H](C)[C@@H](OC)[C@@H](C)C(=O)O)O3)O2)O1] | 13 | 43% | 13% | 82% |
| 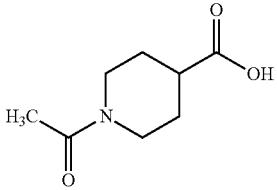 | 14 | 52% | 75% | 67% |
| 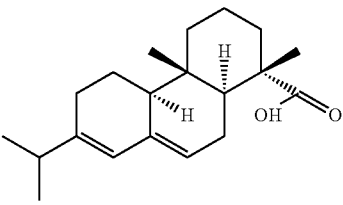 | 15 | 35% | 42% | 22% |
| 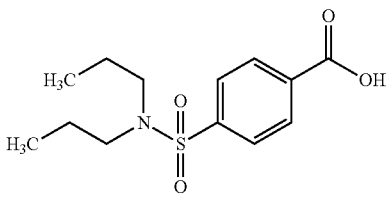 [SMILES: CCCN(CCC)S(=O)(=O)c1ccc(C(=O)O)cc1] | 16 | 55% | 50% | 49% |
| 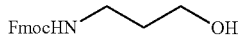 | 17 | 0% | 0% | 0% |
| 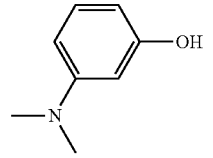 | 18 | 0% | 0% | 0% |

TABLE 1-continued

Enrichment yields of model carboxylic acid-, alcohol-, amine- and thiol-containing molecules with dialkyldisiloxane resin derivatives.

| # | Structure | 9 | 10 |
|---|---|---|---|
| 19 | Cbz-NH-(CH2)4-CH(NH2)-C(O)-OMe | 0% | 0% | 0% |
| 20 | MeO-C(O)-CH(NHBoc)-CH2-SH | 0% | 0% | 0% |

Resin: ●—O—Si(iPr)₂—O—R'

R' (9) = —CH(CH₂Cl)(CH₂Cl)
R' (10) = —CH(CF₃)(CF₃)

| # | Structure | 9 | 10 |
|---|---|---|---|
| 11 | 3-(3-methoxyphenyl)propanoic acid | 95% | 95% |
| 12 | cholic acid | 81% | 47% |
| 13 | monensin-like polyether carboxylic acid | 72% | 80% |
| 14 | 1-acetylpiperidine-4-carboxylic acid | 95% | 90% |

TABLE 1-continued

Enrichment yields of model carboxylic acid-, alcohol-, amine- and thiol-containing
molecules with dialkyldisiloxane resin derivatives.

| Structure | # | Yield 1 | Yield 2 |
|---|---|---|---|
| (abietic acid-like structure with OH, C=O) | 15 | 84% | 63% |
| (dipropylsulfonamide benzoic acid) | 16 | 85% | 69% |
| FmocHN-propyl-OH | 17 | 0% | 0% |
| (3-dimethylamino phenol) | 18 | 0% | 0% |
| Cbz-Lys-OMe (free NH2) | 19 | 0% | 0% |
| Cys(SH)-OMe NHBoc | 20 | 0% | 0% |

Described herein is the use of resins modified with alkoxyl moieties with electron withdrawing groups (EWG) or electron donating groups (EDG). A variety of alcohols, 22 in all, were tested to see which properties (i.e. sterics, EWG, or EDG) yielded resins with the highest loading capacity with three illustrative carboxylic acids (Table S2). The highest loading values were obtained by activation with secondary alcohols. Efficient isolation of tertiary carboxylic acids was only seen with resins derived from electron poor alcohols showing the influence of the leaving group on capture potential (e.g. 9, 10, S23, S24).

TABLE S2

Synthesized diisopropyl disiloxyl resins and their corresponding loading capacities.
Loading capacities of synthesized resins in mmol/g. Each value is an average of four replicates.

| X = | # | 11 | S4 | S8 | Average |
|---|---|---|---|---|---|
| —Cl | 3 | 0.72 | 0.40 | 0.22 | 0.45 |
| —O—CH$_3$ | 6 | 0.10 | 0.12 | 0.04 | 0.09 |
| —O—CH(CH$_3$)$_2$ (isopropoxy) | 7 | 0.31 | 0.16 | 0.04 | 0.17 |

TABLE S2-continued

Synthesized diisopropyl disiloxyl resins and their corresponding loading capacities.
Loading capacities of synthesized resins in mmol/g. Each value is an average of four replicates.

| X = | | 11 | S4 | S8 | Average |
|---|---|---|---|---|---|
| —O—C(CH3)3 (tert-butyl) | 8 | 0.43 | 0.38 | 0.18 | 0.33 |
| —O—CH(CH2Cl)2 | 9 | 0.55 | 0.32 | 0.28 | 0.38 |
| —O—CH(CF3)2 | 10 | 0.45 | 0.28 | 0.12 | 0.28 |
| —O—ethyl | S9 | 0.10 | 0.11 | 0.12 | 0.11 |
| —O—CH2Ph (benzyl) | S10 | 0.01 | 0.01 | 0.01 | 0.01 |
| —O—CH(iBu)2 | S11 | 0.70 | 0.38 | 0.08 | 0.39 |
| —O—9-fluorenyl | S12 | 0.35 | 0.20 | 0.14 | 0.23 |
| —O—cyclopentyl | S13 | 0.30 | 0.15 | 0.12 | 0.19 |
| —O—sec-butyl | S14 | 0.50 | 0.28 | 0.1 | 0.29 |

TABLE S2-continued
Synthesized diisopropyl disiloxyl resins and their corresponding loading capacities.
Loading capacities of synthesized resins in mmol/g. Each value is an average of four replicates.
| X = | | 11 | S4 | S8 | Average |
|---|---|---|---|---|---|
| 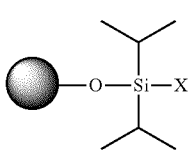 | S15 | 0.22 | 0.10 | 0.10 | 0.11 |
| 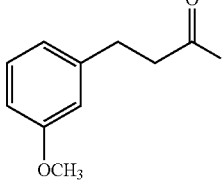 | S16 | 0.30 | 0.14 | 0.11 | 0.18 |
| 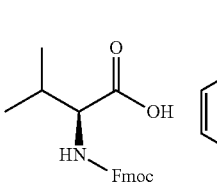 | S17 | 0.011 | 0.020 | 0.013 | 0.015 |
| 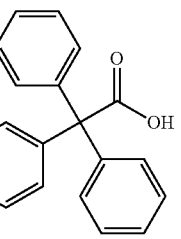 | S18 | 0.16 | 0.010 | 0.10 | 0.10 |
| 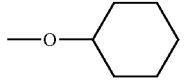 | S19 | 0.55 | 0.32 | 0.1 | 0.32 |
| 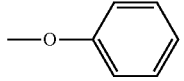 | S20 | 0.31 | 0.21 | 0.10 | 0.20 |
| 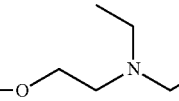 | S21 | 0.19 | 0.22 | 0.10 | 0.16 |
| 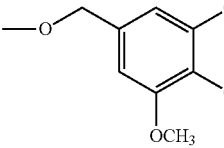 | S22 | 0.030 | 0.030 | 0.030 | 0.030 |
| 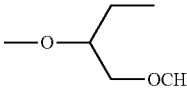 | S23 | 0.31 | 0.25 | 0.26 | 0.27 |
|  | S24 | 0.42 | 0.30 | 0.21 | 0.31 |
| 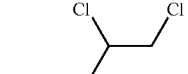 | S25 | 0.13 | 0.10 | 0.11 | 0.11 |

TABLE S2-continued

Synthesized diisopropyl disiloxyl resins and their corresponding loading capacities.
Loading capacities of synthesized resins in mmol/g. Each value is an average of four replicates.

| X = | | 11 | S4 | S8 | Average |
|---|---|---|---|---|---|
| —OH | S26 | 0 | 0 | 0 | 0 |
| —H | S27 | 0 | 0 | 0 | 0 |

From this resin set, 9 and 10 were selected for further characterization based upon both loading capacity and cost of the reagents. These resins were subjected to coupling with a large model set of carboxylic acids ranging in steric hinderance and molecular complexity (20 compounds; Tables 1 and S3). Amine-, thiol- and alcohol-containing compounds were included to assess chemoselectivity (Table 1). High and consistent enrichment yields of a wide array of carboxylic acids were observed with resin 9, which was activated with a 1,3-dichloro-2-propoxyl group. This resin was also found to be completely chemoselective and was selected for use as a carboxylic acid enrichment tag. Interestingly, activation of either the diethylsiloxyl resin (S40) or the diisopropylsilyl resin (S41) as the alkoxyl derivatives produced reagents that were unable to capture any compounds, again supporting the necessity of the diisopropyl siloxyl structure.

TABLE S3

Enrichment yields for resins 6, 7, 8, 9, and 10 with a model set of carboxylic acids.

| | | X = —O—CH$_3$ | —O—CH(CH$_3$)$_2$ | —O—C(CH$_3$)$_3$ | —O—CH(CH$_2$Cl)$_2$ | —O—CH(CF$_3$)$_2$ |
|---|---|---|---|---|---|---|
| | | 6 | 7 | 8 | 9 | 10 |
| Fmoc-NH-CH$_2$-COOH | S28 | 5% | 66% | 50% | 52% | 72% |
| 3-methoxyphenylpropanoic acid | 11 | 25% | 95% | 75% | 95% | 95% |
| (4-methoxyphenyl ketoxime acetic acid) | S29 | 87% | 99% | 70% | 99% | 99% |

TABLE S3-continued

Enrichment yields for resins 6, 7, 8, 9, and 10 with a model set of carboxylic acids.

| Compound | # | 6 | 7 | 8 | 9 | 10 |
|---|---|---|---|---|---|---|
| (cholic acid structure) | 12 | 73% | 94% | 53% | 81% | 47% |
| (indomethacin glycolate structure) | S30 | 0% | 3% | 2% | 15% | 5% |
| (3-cyanophenylacetic acid) | S31 | 82% | 91% | 71% | 88% | 2% |
| (oxo-indane carboxylic acid) | S32 | 44% | 63% | 55% | 89% | 71% |
| (N-acetyl dehydrophenylalanine) | S33 | 71% | 92% | 62% | 99% | 99% |
| (ketoprofen structure) | S34 | 65% | 82% | 64% | 86% | 84% |

TABLE S3-continued

Enrichment yields for resins 6, 7, 8, 9, and 10 with a model set of carboxylic acids.

| Structure | # | 6 | 7 | 8 | 9 | 10 |
|---|---|---|---|---|---|---|
| (complex polyether carboxylic acid) | 13 | 43% | 13% | 82% | 72% | 80% |
| N-acetyl piperidine-4-carboxylic acid | 14 | 52% | 75% | 67% | 95% | 90% |
| Fmoc-Val-OH | S4 | 13% | 74% | 58% | 69% | 81% |
| (podocarpic acid derivative) | S35 | 22% | 22% | 7% | 30% | 8% |
| triphenylacetic acid | S8 | 69% | 99% | 21% | 99% | 93% |

TABLE S3-continued
Enrichment yields for resins 6, 7, 8, 9, and 10 with a model set of carboxylic acids.
| | | 6 | 7 | 8 | 9 | 10 |
|---|---|---|---|---|---|---|
| 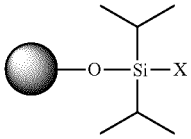 | 15 | 35% | 42% | 22% | 84% | 63% |
| 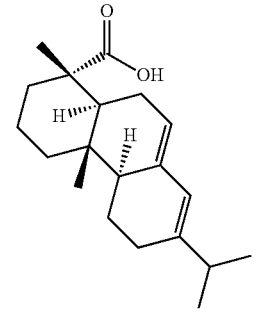 | S36 | 2% | 76% | 70% | 87% | 84% |
| 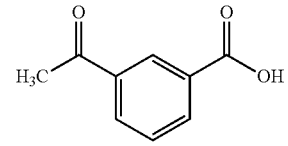 | S37 | 5% | 89% | 75% | 87% | 95% |
| 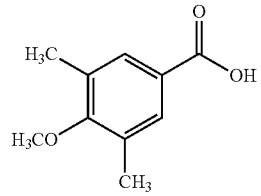 | S38 | 34% | 92% | 75% | 99% | 82% |
| 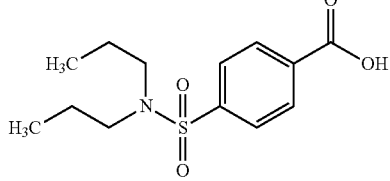 | 16 | 55% | 50% | 49% | 85% | 69% |
| 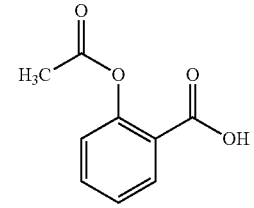 | S39 | 1% | 6% | 5% | 8% | 4% |

The utility of this resin for the isolation of carboxylic acid-containing compounds from complex mixtures is described herein. Monensin (13) is a polyether ionophore antibiotic produced by *Streptomyces cinnamonensis*. [13a] Monensin is secreted into the growth media of this bacterium, which was collected to yield a crude natural product extract. Prior to enrichment, the extract was modified by the addition of four model carboxylic acids and two alcohols, two amines, and a thiol (17-20, S9) to measure enrichment yields and chemoselectivity of an illustrative resin, resin 9, in a biological setting. The crude extract was analyzed by LC-MS.

The extract was subjected to enrichment with resin 9. The resulting material was analyzed by LC-MS using the same gradient. LC-MS analysis showed that monensin (13) was recovered in a 64% yield along with 3-oxo-1-indanecarboxylic acid (S32), 3,5-dimethyl-4-methoxybenzoic acid (S38), probenecid (16), and abietic acid (15) recovered in a 96%, 87%, 75%, and 57% yield, respectively. None of the amine, alcohol, or thiol model compounds were detected, demonstrating that 9 remains highly selective for carboxylic acid-containing compounds in a biological background.

Two alcohols (17, 18), two amines (19, S9), and a thiol (20) were spiked into the extract. LC-MS analysis before enrichment indicates the presence of the spiked compounds. LC-MS analysis showed that none of alcohols (17, 18), amines (19, S9), or the thiol (20) were detectable following capture and release of the extract.

It is evident from the chromatograms that many of highly abundant compounds were eliminated and that fewer compounds are present after carboxylic acid capture, enabling better resolution of the remaining components. Additionally, some features represent a greater proportion of the carboxylic acid fraction than of the crude extract demonstrating enrichment. The extent of carboxylic acid enrichment was quantified in comparison to compounds containing other functional groups that were spiked into the sample. Carboxylic acids were enriched by an average of ~300-fold over other functional groups (Table S5).

TABLE S5

|  | Peak Area Prior to Capture | Peak Area After Capture |
|---|---|---|
| 3-oxo-1-indancarboxylic acid (S32) | 546446 | 478384 |
| probenecid (16) | 3663340 | 2799309 |
| 3,5-dimethyl-4-methoxybenzoic acid (S38) | 1518457 | 1308679 |
| abietic Acid (15) | 2414543 | 1565820 |
| Fmoc-Amino-Propanol (17) | 4455509 | 4559 |
| 3-(dimethylamino)phenol (18) | 4043524 | 21738 |
| trypatmine (S7) | 203403 | 611 |
| H-Lys(Z)-OMe (19) | 36329688 | 453279 |
| Boc-Cys-OMe (20) | 100590 | 2378 |

Additionally, carboxylic acids subjected to resin 9 were enriched ~500-fold in comparison to exposure of the extract to unactivated resin (S27; Table S6).

TABLE S6

| Model Carboxylic Acid | Peak Area Following Exposure to Activated Resin (9) | Peak Area Following Exposure to Unactivated Resin (S27) | Ratio of Enrichment (Activated/ Unactivated resin) |
|---|---|---|---|
| 3-oxo-1-indancarboxylic acid (S32) | 478384 | 1213 | 394 |
| probenecid (16) | 2799309 | 5463 | 512 |
| 3,5-dimethyl-4-methoxybenzoic acid (S38) | 1308679 | 3152 | 415 |
| abietic Acid (15) | 1565820 | 2244 | 698 |

It was found that enrichment occurs equivalently independent of the proportion of the sample that the targeted compounds comprise. Three carboxylic acids were added to the *Streptomyces cinnamonensis* extract at varying concentrations. An average recovery yield of ~80% was observed across ratios of natural product background to targeted acid ranging from 2:1 to 800:1 (8 µmol-15 nmol; Table S7). This shows that the enrichment strategy described herein enables detection of even low abundance species.

TABLE S7

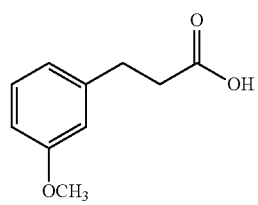 [SMILES: COc1cccc(CCC(=O)O)c1]

11

| mmol of natural product background | mmol of model acid added | Ratio of natural product background to model carboxylic acid (mmol) | Percent Recovery of model carboxylic acid |
|---|---|---|---|
| 0.012 | 0.0076 | 2:1 | 96% |
| 0.012 | 0.00152 | 8:1 | 94% |
| 0.012 | 0.00076 | 16:1 | 94% |
| 0.012 | 0.000152 | 80:1 | 91% |
| 0.012 | 0.000076 | 160:1 | 95% |
| 0.012 | 0.0000152 | 800:1 | 92% |

TABLE S7-continued

| mmol of natural product background | mmol of model acid added | Ratio of natural product background to model carboxylic acid (mmol) | Percent Recovery of model carboxylic acid |
|---|---|---|---|
| | | | S4 (Fmoc-Val-OH structure) |
| 0.012 | 0.0076 | 2:1 | 85% |
| 0.012 | 0.00152 | 8:1 | 95% |
| 0.012 | 0.00076 | 16:1 | 85% |
| 0.012 | 0.000152 | 80:1 | 75% |
| 0.012 | 0.000076 | 160:1 | 78% |
| | | | S8 (triphenylacetic acid structure) |
| 0.012 | 0.0076 | 2:1 | 84% |
| 0.012 | 0.00152 | 8:1 | 91% |
| 0.012 | 0.00076 | 16:1 | 83% |
| 0.012 | 0.000152 | 80:1 | 87% |
| 0.012 | 0.000076 | 160:1 | 83% |

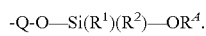

The dynamic range of the capture efficiency of resin 9 in a background of a crude natural product mixture is shown above in Table S7. The average molecular weight of the extract material was assumed to be 350 g/mol for the purpose of calculation of "mmol of natural product background."

The utility of resin 9 for isolation of carboxylic acids following solution phase synthesis is also described herein. The methyl ester of serine was converted to the corresponding carboxylic acid and the crude reaction reacted with 9, washed, and released, resulting in isolation of the product in good yield and high purity. This demonstrates that the resins and methods described herein can be used to purify synthetically-derived carboxylic acids, mostly notably, polar compounds that are difficult to isolate using standard chromatography methods.

Described herein is the synthesis of chemoselective enrichment tags for the isolation of carboxylic acid-containing molecules and its application to the enrichment of carboxylic acids from a variety of mixture types.

Several illustrative embodiments of the invention are described by the following enumerated clauses:

1. A polymeric reagent for use in the selective enrichment of carboxyl group-containing compounds from a mixture:
comprising a polymer having one or more functional groups of formula -Q-O—Si($R^1$)($R^2$)—O$R^4$.

wherein
the functional group is capable of reacting with the carboxyl group-containing compounds when the mixture containing the compounds contacts the reagent;

Q is alkylene or heteroalkylene, each of which is optionally substituted;
$R^1$ is $C_1$-$C_8$ alkyl or $C_3$-$C_8$ cycloalkyl;
$R^2$ is $C_1$-$C_8$ alkyl or $C_3$-$C_8$ cycloalkyl; and
$R^4$ is selected from the group consisting of alkyl, heteroalkyl, aryl, heteroaryl, arylalkyl, heteroarylalkyl, arylheteroalkyl, and heteroarylheteroalkyl, each of which is optionally substituted.

2. The polymeric reagent of clause 1, wherein the functional group is attached to a main chain or side chain of the polymer by a linking group.

3. The polymeric reagent of clause 1 or 2 wherein the linking group is a phenylene group.

4. The polymeric reagent of any one of the preceding clauses wherein the linking group is a para-phenylene group.

5. The polymeric reagent of any one of the preceding clauses wherein $R^1$ is $C_1$-$C_8$ alkyl; and $R^2$ is $C_1$-$C_8$ alkyl.

5a. The polymeric reagent of any one of the preceding clauses wherein each of $R^1$ and $R^2$ is isopropyl.

6. The polymeric reagent of any one of the preceding clauses wherein Q is heteroalkylene.

7. The polymeric reagent of any one of the preceding clauses wherein Q is $CH_2$—O—$(CH_2)_n$C$(CH_3)_2$ wherein n is an integer from about 1 to about 5.

8. The polymeric reagent of clause 7 wherein n is 2.

9. The polymeric reagent of any one of the preceding clauses wherein the polymer is a polyolefin, polyamide, polyurethane, or polycarbonate.

10. The polymeric reagent of any one of the preceding clauses wherein the polymer is a polyolefin.

11. The polymeric reagent of any one of the preceding clauses wherein the polymer is a polystyrene.

12. The polymeric reagent of any one of the preceding clauses wherein the polymeric reagent is a polystyrene of formula

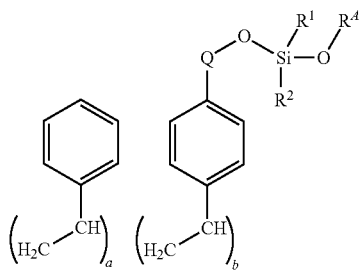

wherein the ratio of b to a is from about 1:99 to about 1:1, and wherein the polystyrene is crosslinked with from 0.5 to 10.0% divinylbenzene.

13. The polymeric reagent of any one of the preceding clauses wherein the functional group is $CH_2OCH_2CH_2C(CH_3)_2OSiR^1R^2OR^4$.

13a. The polymeric reagent of any one of the preceding clauses wherein $R^1$ is branched $C_1$-$C_8$ alkyl; and $R^2$ is branched $C_1$-$C_8$ alkyl.

14. The polymeric reagent of any one of the preceding clauses wherein $R^1$ and $R^2$ are each iso-propyl.

15. The polymeric reagent of any one of the preceding clauses wherein $R^4$ is haloalkyl.

16. The polymeric reagent of any one of the preceding clauses wherein $R^4$ is 1,3-dichloro-2-propyl.

17. A process for preparing a second mixture selectively enriched in carboxyl group containing compounds from a first mixture containing the carboxyl group-containing compounds, the method comprising the step of
(a) contacting the first mixture with the polymeric reagent of any one of clauses 1 to 16;
wherein one or more of the functional groups forms a covalent bond with the carboxyl group of one or more of the carboxyl group-containing compounds.

18. The process of clause 17 further comprising the step (b) of washing the polymer resulting from step (a) with a solvent selected from the group consisting of optionally branched $C_5$-$C_{10}$ alkanes, optionally-branched $C_1$-$C_5$ alcohols, benzene, toluene, xylenes, $C_1$-$C_5$ alkyl $C_2$-$C_5$ alkanoates, where each of the alkyl or the alkanoate is optionally branched, $C_1$-$C_4$ alkylnitriles, DMF, THF, dioxane, DMSO, $C_1$-$C_4$ haloalkanes, and combinations thereof.

19. The process of clause 17 or 18 further comprising the step (c) of cleaving the covalent bond between the functional group and the carboxyl group-containing compound.

20. The process of any one of the preceding clauses wherein the first mixture is an extract of plant material, an extract of a fermentation broth, or a mixture resulting from a process to prepare one or more carboxyl group-containing compounds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like. It is to be understood that an alkyl group may be attached to other portions of a structure containing the alkyl group by one or more covalent bonds.

As used herein, the term "alkylene" includes a bivalent chain of carbon atoms, which is optionally branched, having two attachment points that may be on adjacent or non-adjacent carbons. It is to be further understood that in certain embodiments, alkylene is advantageously of limited length, including $C_1$-$C_{24}$, $C_1$-$C_{12}$, $C_1$-$C_8$, $C_1$-$C_6$, and $C_1$-$C_4$. It is appreciated herein that shorter alkylene groups may add less lipophilicity to the compound and accordingly will have different pharmacokinetic behavior.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "heteroalkylene" includes a chain of atoms that includes both carbon and at least one heteroatom, and is optionally branched, having two attachment points that may be on adjacent or non-adjacent atoms. Illustrative heteroatoms include nitrogen, oxygen, and sulfur. In certain variations, illustrative heteroatoms also include phosphorus, and selenium.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical —$(CH_2)_xZX$, where x is an integer from 0-6 and ZX is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or ZX is selected from —$CO_2R^4$ and —$CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

Methods
Resin Synthesis

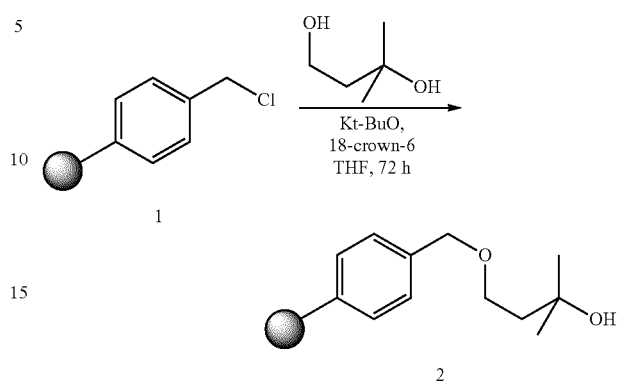

To a 50 mL oven-dried round bottom flask was added 25 mL of anhydrous THF and 2.0 g (2.1 mL, 19 mmol, 3.0 eq) of 3-methyl-1,3-butanediol. This solution was placed under Ar and cooled to 0° C. in an ice bath. Next, a 1 M solution of potassium t-butoxide (2.2 g, 19 mmol, 3.0 eq) in THF (20 mL) was added followed by 5.2 g (19 mmol, 3.0 eq) of 18-crown-6. This mixture was stirred for 1 h at 0° C. and then 3 h at room temperature. During the warm-up to room temperature, the solution turned from clear to light yellow. This yellow solution was then transferred via syringe to a 250 mL amber bottle with a rubber septum where 5.0 g of Merrifield resin (1.6 mmol/g) and 20 mL of THF had been placed and allowed to swell under Ar for 2 h. This resin suspension was capped and allowed to shake for 72 h at room temperature. The golden resin was then transferred to a peptide synthesis vessel with THF. The resin was subjected to the following wash protocol: THF (2×20 mL), DMF (3×10 mL), 1:1 DMF:$H_2O$ (3×100 mL), DMF (3×100 mL), THF (3×100 mL), and $CH_2Cl_2$ (3×100 mL). The vessel was placed in a desiccator under vacuum for 12 h to dry the resin.

A 20 mL scintillation vial was charged with 200 mg (0.26 mmol) of 2 (loading capacity 1.6 mmol/g) and equipped with a rubber septum. After flushing the resin with Ar for 10 minutes, the vial was charged with 3 mL of anhydrous $CH_2Cl_2$ and the resin was allowed to swell for 5 min. To the swollen resin was added 263 μL (1.8 mmol, 7.0 eq) of freshly distilled $Et_3N$, 160 μL (1.3 mmol, 5.0 eq) of dichlorodiisopropyl silane and 318 mg (2.9 mmol, 10.0 eq) of DMAP. The vial was then capped and the reaction was agitated for 16 h at room temperature. The resin was filtered over a 10 mL fritted polypropylene column and washed with 2×4 mL anhydrous CH₂Cl₂ and used immediately to avoid undesired hydrolysis.

Alcoholysis Procedure

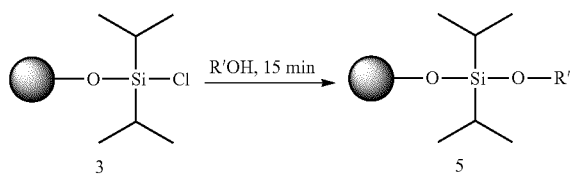

Before rinsing 3 with anhydrous CH₂Cl₂ to remove excess Et₃N and DMAP, 500 μL or 500 mg of an alcohol was added and the vial re-capped. This promoted the hydrolysis of the Si—Cl bond to the corresponding siloxyl ether. After agitation for 15 min at room temperature, the resin was rinsed with 2×5 mL anhydrous CH₂Cl₂. The resin was then re-swollen in 2.5 mL of CH₂Cl₂ and measured into 5 different vials (4 reaction and 1 discard vial).

Coupling Procedure

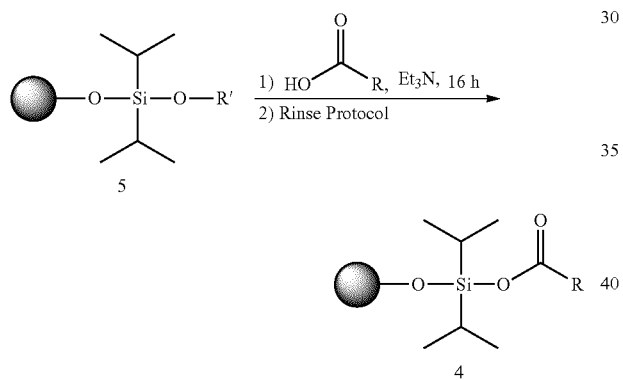

To 5 (40 mg 0.015 mmol) was added 50 μL of freshly distilled Et₃N (0.35 mmol, 20 eq) followed by 100 μL of a mixture of model carboxylic acids in a DMSO/THF solution. The solution contained four carboxylic acids, 0.1 equivalent of each, and 400 μL of anhydrous THF and 100 μL of DMSO. The coupling reactions were gently agitated at room temperature overnight. The resin was transferred to a 2 mL fritted polypropylene column and subjected to the standard wash protocol.

Cleavage of Model Carboxylic Acids from Resin

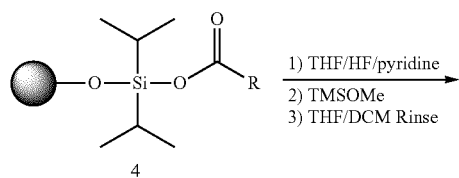

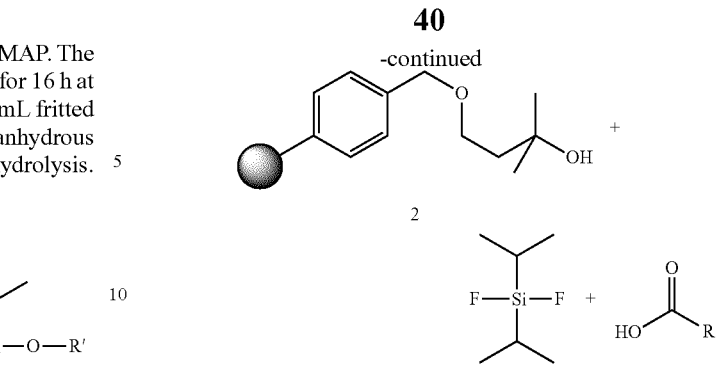

Coupled resin was transferred to polypropylene vials (2 mL). To the resin was added 100 μL of a freshly prepared solution of 500/50/50 μL (v/v) of THF/HF.pyridine (70/30 wt %)/pyridine (2 mmol of HF, 45 eq) and the reaction was gently agitated at room temperature for 3 h. To this was added 500 μL of TMSOMe (3.6 mmol, 82 eq) to quench excess HF and the resin was agitated for an additional 30 minutes at room temperature. The resin was washed with THF and CH₂Cl₂ and filtered over a 1 mL fritted polypropylene column into a 5 mL vial. This solution was then concentrated and the sample was analyzed by dissolving the sample in 2 mL of 2:1:1 H₂O/THF/MeOH and injecting 1 μL onto a LC-MS-TOF and comparing peak area to the corresponding standard curve data.

Standard Resin Wash Protocol.

Coupled resin (40 mg) is transferred to a fritted vessel and rinsed as follows: CH₂Cl₂ (suspend resin in 2 mL for 10 min, rinse 2×2 mL), THF (suspend resin in 2 mL for 10 min, rinse 2×2 mL), DMSO/CH₂Cl₂ (1:1, suspend resin in 2 mL for 10 min, rinse 2×2 mL), THF (suspend resin in 2 mL for 10 min, rinse 2×2 mL), DMSO/CH₂Cl₂ (1:1, suspend resin in 2 mL for 10 min, rinse 2×2 mL), CH₂Cl₂ (suspend resin in 2 mL for 10 min, rinse 2×2 mL), toluene (3×2 mL), DMF (3×2 mL), CH₂Cl₂ (3×2 mL), hexanes (3×2 mL), CH₂Cl₂/MeOH (3×2 mL), CH₂Cl₂ (3×2 mL). The resin is then allowed to dry in a vacuum desiccator for at least 1 h before HF cleavage.

Determination of Resin Loading Capacity.

For each of the resins, 200 mg (1.3 mmol/g, 0.26 mmol) was placed in a dry 20 mL scintillation vial. The resin was swollen with 3 mL of anhydrous CH₂Cl₂ under Ar. Next, 300 μL (8.0 equiv, 2.1 mmol) of freshly distilled Et₃N was added, followed by 250 μL (6.0 equiv, 1.7 mmol) of dichlorodiisopropyl silane. 318 mg of DMAP (10.0 equiv, 2.6 mmol) was added and the vial was capped and allowed to agitate at room temperature for 16 h. For resins 6-10 and S9-S26, after overnight reaction with the silane, 500 mg or 500 μL of the corresponding alcohol was added, the vial was re-capped, and allowed to agitate for 15 additional min at room temperature. The resin was transferred to a 10 mL biospin vial and rinsed under Ar with anhydrous CH₂Cl₂ (2×2 mL). Next, 2.5 mL of anhydrous CH₂Cl₂ was added to the resin and allowed to swell for 1 min. The resin was aliquoted into five 2 mL vials (40 mg of resin into each). Four aliquots acted as replicate reactions and the fifth was discarded. A control resin was synthesized utilizing chlorodiisopropylsilane (S27) (same equiv as previously mentioned), which had no appropriate leaving group. To each of the vials was added 50 μL (0.7 mmol) of freshly distilled Et₃N and 3.0 equiv (as compared to the assumed loading capacity of the resin; 0.16 mmol for each resin aliquot) of a model acid dissolved in 500 μL of anhydrous THF. The reactions were agitated overnight at room temperature. Resin was transferred to a 2 mL biospin vessel and subjected to the standard wash protocol. The resins were dried for 1 h at room temperature in a vacuum desiccator at 30 mmHg. Coupled resin was then transferred to polypropylene vials (2 mL). To the resin was added 500/50/50 μL (v/v) of a freshly prepared solution of THF/HF.pyridine (70/30 wt %)/pyridine (1.6 mmol of HF) and the reaction was gently agitated at room temperature for 3 h. To this was added 500 μL of TMSOMe (3.6 mmol) to quench excess HF and the resin was agitated for an additional 30 min at room temperature. The resin was washed with THF (3×1 mL) followed by $CH_2Cl_2$ (3×1 mL) and filtered over a 1 mL fritted polypropylene column into a 5 mL vial. The rinse was concentrated under reduced pressure with no additional heating and the sample was redissolved in 5 mL of 2:1:1 $H_2O$/THF/MeOH. Analysis was performed by injection of 1 μL of this solution onto a LC-MS-TOF and comparing the observed peak area to that of standard curve data. The average of the four replicates was used as the loading capacity for all subsequent coupling experiments. The loading capacity for all 25 synthesized resins is shown in Table S2.

Demonstration of Resin Regeneration.

Each resin was coupled as in the Loading Capacity Experiment section, with the exception that the resins had previously been coupled to acids and subjected to cleavage conditions resulting in regeneration of 2. Averaging of four replicates gave the loading capacities as shown below in Table S4.

Demonstration of the regenerative properties of the developed capture resins. This resin can be re-used for multiple cycles without a substantial decrease in loading capacity.

Ratios of enrichment of carboxylic acids compared to those molecules with no carboxylic acid moiety are shown in Table S5. To illustrate that the carboxylic acid-containing compounds are enriched in comparison to the molecules containing other functional groups, the ratio of enrichment was calculated. The ratio of each carboxylic acid to the chemoselective set of compounds was calculated and normalized. Normalization is required given that although an equivalent number of moles of each compound were used, the ionization efficiency of each compound is unique, making the observed peak areas dramatically different. Accordingly, the initial ratios were normalized to a 1:1 ratio and this factor was applied to the post-capture data. In all cases, following the capture and release protocol at least a 63-fold enrichment of the carboxylic acids was seen in comparison to the non-carboxylic acid compounds. These data were obtained from the *Streptomyces cinnamonensis* extract enrichment experiment.

TABLE S4

| 3 | 11 | S4 | S8 | Average |
|---|---|---|---|---|
| Initial | 0.72 | 0.40 | 0.22 | 0.45 |
| Recycled | 0.70 | 0.38 | 0.24 | 0.44 |

| 8 | 11 | S4 | S8 | Average |
|---|---|---|---|---|
| Initial | 0.43 | 0.38 | 0.18 | 0.33 |
| Recycled | 0.46 | 0.31 | 0.22 | 0.33 |

| 9 | 11 | S4 | S8 | Average |
|---|---|---|---|---|
| Initial | 0.55 | 0.32 | 0.28 | 0.38 |
| Recycled | 0.49 | 0.27 | 0.27 | 0.34 |

TABLE S5

| Compounds | Peak Area Prior to Capture | Peak Area After Capture |
|---|---|---|
| 3-oxo-1-indancarboxylic acid (S32) | 546446 | 478384 |
| probenecid (16) | 3663340 | 2799309 |
| 3,5-dimethyl-4-methoxybenzoic acid (S38) | 1518457 | 1308679 |
| abietic Acid (15) | 2414543 | 1565820 |
| Fmoc-Amino-Propanol (17) | 4455509 | 4559 |
| 3-(dimethylamino)phenol (18) | 4043524 | 21738 |
| trypatmine (S7) | 203403 | 611 |
| H-Lys(Z)-OMe (19) | 36329688 | 453279 |
| Boc-Cys-OMe (20) | 100590 | 2378 |

| Compounds | Peak Ratio Before Capture | Normalization Factor | Peak Ratio After Capture | Normalized Ratio After Capture |
|---|---|---|---|---|
| S32:17 | 0.12 | 8.15 | 104.93 | 855.57 |
| S32:18 | 0.14 | 7.40 | 22.01 | 162.84 |
| S32:S7 | 2.69 | 0.37 | 782.95 | 291.44 |
| S32:19 | 0.02 | 66.48 | 1.06 | 70.17 |
| S32:20 | 0.55 | 1.83 | 201.17 | 368.36 |
| S38:17 | 0.34 | 2.93 | 287.05 | 842.28 |
| S38:18 | 0.38 | 2.66 | 60.20 | 160.31 |
| S38:S7 | 7.47 | 0.13 | 2141.86 | 286.91 |
| S38:19 | 0.04 | 23.93 | 2.89 | 69.08 |
| S38:20 | 1.52 | 0.66 | 550.33 | 362.64 |
| 16:17 | 0.82 | 1.22 | 614.02 | 746.79 |
| 16:18 | 0.91 | 1.10 | 128.77 | 142.14 |
| 16:S7 | 18.01 | 0.06 | 4581.52 | 254.38 |
| 16:19 | 0.10 | 9.92 | 6.18 | 61.24 |
| 16:20 | 3.66 | 0.27 | 1177.17 | 321.53 |

TABLE S5-continued

| | | | | |
|---|---|---|---|---|
| 15:17 | 0.54 | 1.85 | 343.46 | 633.77 |
| 15:18 | 0.60 | 1.67 | 72.03 | 120.63 |
| 15:S7 | 11.87 | 0.08 | 2562.72 | 215.89 |
| 15:19 | 0.07 | 15.05 | 3.45 | 51.98 |
| 15:20 | 2.41 | 0.41 | 658.46 | 272.87 |

| Compounds | Average of Enrichment Ratio |
|---|---|
| Carboxylic Acid to Primary Alcohol | 770 |
| Carboxylic Acid to Phenol | 147 |
| Carboxylic Acid to Primary Amine | 262 |
| Carboxylic Acid to Secondary Amine | 63 |
| Carboxylic Acid to Thiol | 331 |

Ratios of enrichment of carboxylic acids subjected to activated resin versus unactivated resin are shown above in Table S6. The *Streptomyces cinnamonensis* extract (containing the full chemoselective set and four additional acids) was subjected separately to activated resin (9) and an unactivated control (S27). The peak areas obtained following performance of the release protocol from both resin samples are shown above. These results illustrate that the observed enrichment of the acids is a result of selective capture by the activated disiloxane moiety and not due to non-specific binding to the resin.

The dynamic range of the capture efficiency of resin 9 in a background of a crude natural product mixture is shown above in Table S7. The average molecular weight of the extract material was assumed to be 350 g/mol for the purpose of calculation of "mmol of natural product background."

TABLE S8

| Molecule | | Recovery Yield from Extraction of Basic Fraction | Recovery Yield from Extraction of Acidic Fraction | Recovery Yield Utilizing Resin 9 |
|---|---|---|---|---|
| 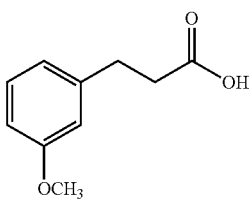 [SMILES: COc1cccc(CCC(=O)O)c1] | 11 | 0% | 40% | 95% |
| 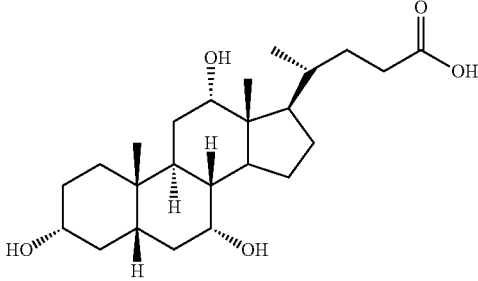 | 12 | 0% | 83% | 81% |

TABLE S8-continued
| Molecule | | Recovery Yield from Extraction of Basic Fraction | Recovery Yield from Extraction of Acidic Fraction | Recovery Yield Utilizing Resin 9 |
|---|---|---|---|---|
| 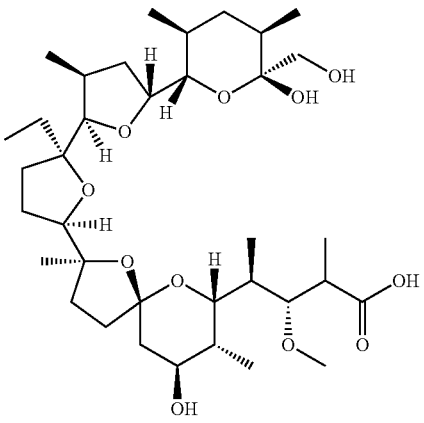 [SMILES: CC[C@@]1([C@@H]2O[C@@H]([C@H]3O[C@@](O)(CO)[C@H](C)C[C@@H]3C)C[C@@H]2C)CC[C@H]([C@]2(C)CC[C@]3(C[C@H](O)[C@@H](C)[C@@H]([C@@H](C)[C@@H](OC)C(C)C(=O)O)O3)O2)O1] | 13 | 34% | 0% | 72% |
| Compounds Containing Functional Groups Not Enriched With Resin 9 | | | | |
| 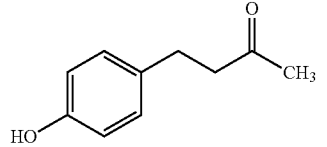 | S42 | 61% | 0% | ND* |
| 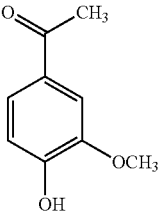 | S43 | 0% | 64% | ND* |
| 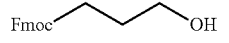 | 17 | 49% | 0% | 0% |
| 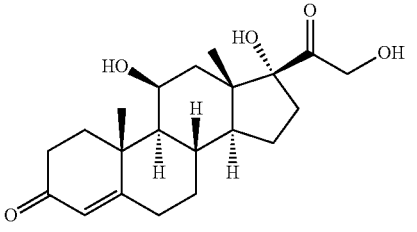 | S44 | 20% | 0% | ND* |
| 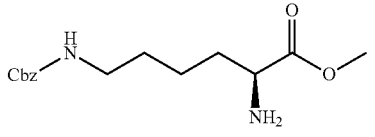 [SMILES: COC(=O)[C@@H](N)CCCCNC(=O)OCc1ccccc1] | 19 | 69% | 0% | 0% |
| 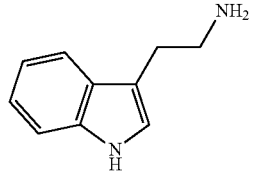 [SMILES: NCCc1c[nH]c2ccccc12] | S7 | 23% | 0% | 0% |

TABLE S8-continued

| Molecule | Recovery Yield from Extraction of Basic Fraction | Recovery Yield from Extraction of Acidic Fraction | Recovery Yield Utilizing Resin 9 |
|---|---|---|---|
| 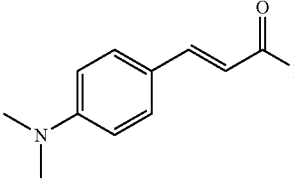 S45 | 20% | 0% | ND* |

*ND = these molecules do not contain a carboxylic acid moiety and would not be captured and released by 9. It is believed that these yields would be negligible.

A comparison of the recovery yields obtained from performing a standard acid/base organic extraction to yields achieved utilizing resin 9 is shown above in Table S8. Broth obtained from growth of *Streptomyces cinnamonensis* was spiked with model compounds. It was made basic (pH 10.5) and extracted and then acidified (pH 2.5) and extracted again. As expected, carboxylic acids 11 and 12 were found in the material extracted following acidification of the aqueous broth. Although monensin (13) contains a carboxylic acid, it was present in the organic layer obtained following extraction of the basified broth. This is likely due to its relatively hydrophobic character and highlights the utility of a strategy to enrich all compounds containing this functional group regardless of their solubility properties. Application of 9 to the isolation of carboxylic acid-containing compounds resulted in similar or better yields than those obtained by organic extraction (11-13). Compounds that would not be enriched with resin 9 were also examined. Amines (19, S7, S45) and alcohols (17, S44) were found in the extraction from the basic fraction as expected. Phenol-containing compounds (S42, S43) were present in the organic layer following extraction of both the basic and the subsequently acidified broth, suggesting that these compounds were parsed based upon both acidity and hydrophobicity.

Preparation of *Streptomyces Cinnamonensis* Extract.

*Streptomyces cinnamonensis* was purchased from ATCC as a freeze-dried pellet. Cell cultures were started utilizing 5 mL of ISP Medium 1. After 3 days of incubation at 28° C. at 175 rpm, these 5 mL cultures were transferred to 100 mL of ISP Medium 1 and again incubated for 3 days under the previous conditions. Finally, the 100 mL cultures were transferred to 4 L flasks that contained 1 L of ISP Medium 1. These cultures were incubated for 7 days. After this time, the culture was transferred to Nalgene centrifuge vessels and spun at 7000 rpm for 35 min. The broth was decanted from the cell pellet into a 2 L flask. To the broth was then added 10 g of XAD-16 resin. The flask was then shaken at 175 rpm overnight. The resin was transferred to a 500 mL peptide synthesis vessel and rinsed with 100 mL of $H_2O$ X 2. The resin was then subjected to the following wash protocol to elute off all compounds from the resin: MeOH 100 mL, ACN 100 mL, EtOAc 100 mL, Acetone 100 mL, EtOAc 100 mL, ACN 100 mL, MeOH 100 mL. The washes were combined and concentrated to yield 297 mg of crude material. From the extract, it was determined via LC-MS-TOF analysis that the sample contained 46 nmol of Monensin per 1 mg of crude material.

Enrichment of Endogenously Produced Monensin (13).

Bacterial extract material (12 mg) was dissolved in 600 µL of anhydrous THF and 500 µL of anhydrous DMSO. The chemoselective compound mixture (1.9 mL solution containing 46 nmol each of Boc-Cys-OMe, tryptamine, H-Lys(Z)-OMe, Fmoc-aminopropanol, 3-(dimethylamino)phenol, 3-oxo-1-indancarboxylic acid, probenecid, 3,5-dimethyl-4-methoxy-benzoic acid, and abietic acid in 90% THF/10% DMSO) was added, which brought the total volume of the solution to 3 mL. Six 2 mL vials were charged with 40 mg ("3 equivalents"; see below) of 9, which was synthesized as previously described. The resin was then swollen in 500 µL of DCM and 300 µL of $Et_3N$ was added, followed by 500 µL of the above extract/chemoselective solution. This amount of resin was chosen by estimation of the theoretical number of moles of material in the bacterial extract based on the assumption that the average compound molecular weight was 350 Da. The vials were capped and agitated overnight at room temperature. The resin was transferred to 2 mL biospin vessels and subjected to the wash protocol described previously. The resin vessels were dried for 1 h in a vacuum desiccator at 30 mmHg. The dried resin was transferred to 2 mL polypropylene vials and swollen with 500 µL of anhydrous THF. To each vial was added 100 µL of a 50/50 mixture (v/v) of HF/pyridine (70/30 wt %)/pyridine. The vials were capped and agitated for 3 h at room temperature. After this time, 500 µL of TMSOMe was added to quench excess HF and the resin was agitated for an additional 30 min at room temperature. The resin was washed with THF (3×2 mL), DCM (3×2 mL), and filtered over a 2 mL fritted polypropylene column into a 5 mL vial. This solution was then concentrated under reduced pressure with no heating and the sample was dissolved in 200 µL of 2:1:1 $H_2O$/THF/MeOH. Analysis was performed by injection of 5 µL of this solution onto a LC-MS-TOF and comparing the observed peak area to that of standard curve data. LC-MS analysis showed that monensin (13) was recovered in a 64% yield along with 3-oxo-1-indane-carboxylic acid (S32), 3,5-dimethyl-4-methoxybenzoic acid (S38), probenecid (16), and abietic acid (15) recovered in a 96%, 87%, 75%, and 57% yield, respectively. None of the amine, alcohol, or thiol model compounds were detected, demonstrating that 9 remains highly selective for carboxylic acid-containing compounds in a biological background.

Organic Extraction of Model Compounds from a Crude Broth Background 15 mg of a crude extract of the concentrated broth from *Streptomyces cinnamonensis* was dissolved in 50 mL of a 3% $NH_4OH$ solution (pH=10.5). To this was spiked in 0.5 mg of 11, 12, 13, S42, S43, 17, S44, 19, S7, and S45. This basic aqueous layer was extracted three times with 50 mL of ethyl acetate. These organic layers were then combined and concentrated. The basic organic layer was then acidified using concentrated HCl (approximately 2 mL) to yield an aqueous phase with a pH of 2.5. This acidic aqueous layer was extracted three times with 50 mL of ethyl acetate. The organic layers were combined and concentrated. Recovery yields were calculated for all model compounds after dissolving the resulting pools in 3 mL of 50/25/25 $H_2O$/THF/MeOH, injecting 1 μL of this solution onto an LC-MS-TOF, and comparing the corresponding ion peak areas to those obtained from a standard curve. These yields are shown in Table S8. Extraction protocol adapted from Natural Products Isolation. Ed. Sarker, S. D.; Latif, Z.; Gray, A. I. Humana Press Inc., Totowa, N.J., 2006.

Protocol for Acquisition, Analysis, and Calculation of Enrichment Yields Using LC-MS-TOF Spectral Data.

For each model compound, a standard curve was generated from solutions with known concentrations. All compounds were dissolved in 2:1:1 $H_2O$:MeOH:THF to yield the concentrations required to provide 1000 pmol, 700 pmol, 560 pmol, 420 pmol, 280 pmol, 140 pmol, and 1 pmol in separate 1 μL injections into the LC-MS-TOF. For all compounds, the optimal fragmentation voltage for the desired ion was determined by assessment of the 700 pmol injection at 50V, 100V, 125V, 150V, 175V, 200V, 225V, and 250V. The fragmentation voltage yielding the highest ion intensity was selected. Following this analysis, all samples were run at each optimal voltage determined for each compound included in the sample. Standard curves were generated for all model compounds by running two independent sets of samples. Unknown samples were quantified by comparison to the generated standard curves. All reactions were run in quartet. The average number of pmoles obtained from the capture and release of each model compound was compared to the initial pmoles added to the reaction giving an enrichment yield as a percentage (i.e., moles obtained following capture and release divided by moles initially added to the experiment).

Saponification Reaction

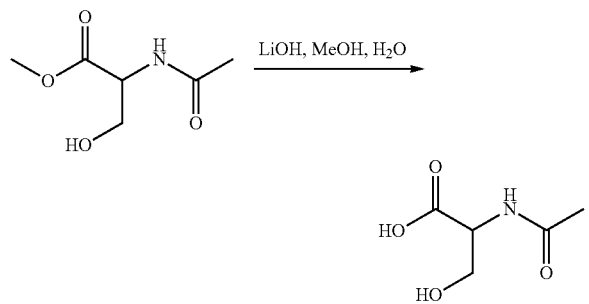

To a 25 mL roundbottom flask was added 20 mg of Ac-Ser-OMe (1.0 equiv, 0.12 mmol) dissolved in 5 mL of MeOH and 1 mL of $H_2O$. Next, 30 mg of LiOH (0.24 mmol, 2.0 equiv) was added to the flask and stirred for 30 min. The crude reaction mixture was concentrated to yield a mixture of Ac-Ser-OMe (starting material), Ac-Ser-OH (product), excess LiOH, and other reaction by-products. TIC of the crude saponification reaction mixture showed that both starting material ($t_R$=0.35 min) and product ($t_R$=0.56 min) are present. The TIC of the carboxylic acid-enriched sample showed only the presence of the product. This crude mixture was dissolved in 4 mL of THF and 1 mL of DMSO and subjected to coupling conditions with 500 mg of 9 as described. After agitating the resin overnight, it was subjected to the standard wash protocol, dried for 1 h in a vacuum dessicator at 30 mmHg, and subjected to the cleavage conditions using HF/pyridine/pyridine as described previously. After quenching the excess HF with TMSOMe, the resin was washed twice with 2 mL of THF and once with 2 mL of $CH_2Cl_2$. This solution was concentrated to yield only the corresponding product of this saponification reaction (15 mg, 83% purified yield) as determined by LC-MS-TOF analysis.

$^1$H NMR comparison of monensin standard before and after treatment with HF/pyridine cleavage conditions (pH~3.5) showed that the HF/pyridine cleavage conditions did not lead to a detectable amount of epimerization of the spiroketal moiety. The spiroketal portion of monensin has been reported to be acid sensitive resulting in epimerization. Epimerization results in dramatic changes in both chemical shift values and coupling patterns of the observed protons in this region (3.80 to 4.10 ppm), which are not observed, indicating that no epimerization has occurred.

Resin Characterization Data.

2: FT-IR (on-bead KBr pellet) $v_{max}$: 3466, 3059, 2849, 1384, 1149, 1087 cm$^{-1}$; gel phase $^{13}$C NMR (125 MHz, CDCl$_3$) δ 73.1, 70.4, 67.4, 41.4, 40.3, 29.3

3: FT-IR (on-bead KBr pellet) $v_{max}$: 3025, 2920, 1057, 883, 611 cm$^{-1}$; gel phase $^{13}$C NMR (125 MHz, CDCl$_3$) δ 76.4, 73.3, 67.5, 44.5, 41.0, 30.4, 17.6, 16.8

6: FT-IR (on-bead KBr pellet) $v_{max}$: 3060, 2973, 2930, 1012, 882 cm$^{-1}$; gel phase $^{13}$C NMR (125 MHz, CDCl$_3$) δ 73.6, 67.9, 51.3, 44.8, 41.0, 30.7, 18.2, 18.1, 13.8

7: FT-IR (on-bead KBr pellet) $v_{max}$: 3059, 2922, 1028, 880 cm$^{-1}$; gel phase $^{13}$C NMR (125 MHz, CDCl$_3$) δ 76.4, 73.5, 67.6, 65.3, 44.5, 41.0, 30.7, 30.4, 26.4, 18.3, 18.2 14.3

8: FT-IR (on-bead KBr pellet) $v_{max}$: 3082, 2935, 1046, 906 cm$^{-1}$; gel phase $^{13}$C NMR (125 MHz, CDCl$_3$) δ 76.3, 73.4, 67.6, 44.5, 41.0, 30.4, 17.6, 16.8

9: FT-IR (on-bead KBr pellet) $v_{max}$: 3058, 2855, 1153, 882, 695 cm$^{-1}$; gel phase $^{13}$C NMR (125 MHz, CDCl$_3$) δ 76.3, 73.8, 71.9, 67.6, 46.1, 44.5, 41.0, 30.9, 30.4, 18.0, 17.9, 17.6, 16.8, 14.3

10: FT-IR (on-bead KBr pellet) $v_{max}$: 3025, 2926, 1264, 1223, 1068, 818 cm$^{-1}$; gel phase $^{13}$C NMR (125 MHz, CDCl$_3$) δ 121.3, 76.4, 75.3, 73.8, 67.5, 44.5, 41.0, 30.9, 30.4, 18.0, 17.9, 17.7, 16.8, 14.3

S9: FT-IR (on-bead KBr pellet) $v_{max}$: 3061, 2924, 1088, 885 cm$^{-1}$; gel phase $^{13}$C NMR (125 MHz, CDCl$_3$) δ 73.6, 67.8, 58.9, 44.8, 41.0, 30.7, 19.0, 18.3, 18.2, 14.0

S10: FT-IR (on-bead KBr pellet) $v_{max}$: 3026, 2925, 1025, 883 cm$^{-1}$; gel phase $^{13}$C NMR (125 MHz, CDCl$_3$) δ 142.0, 128.7, 127.4, 126.5, 73.8, 67.8, 65.1, 44.8, 41.0, 30.8, 18.3, 18.2, 14.0

S11: FT-IR (on-bead KBr pellet) $v_{max}$: 3024, 2929, 1099, 884; gel phase $^{13}$C NMR (125 MHz, CDCl$_3$) δ 76.4, 73.3, 67.4, 56.4, 44.5, 41.0, 30.4, 23.4, 17.6, 16.8

S12: FT-IR (on-bead KBr pellet) $v_{max}$: 3025, 2926, 1748, 1061 cm$^{-1}$; gel phase $^{13}$C NMR (125 MHz, CDCl$_3$) δ 146.8, 140.5, 129.1, 128.0, 126.0, 120.3, 76.3, 75.9, 74.4, 67.6, 44.5, 41.0, 30.9, 18.4, 17.9, 17.6, 16.8, 14.9, 14.3

S13: FT-IR (on-bead KBr pellet) $v_{max}$: 3059, 2965, 1601, 1053, 882 cm$^{-1}$; gel phase $^{13}$C NMR (125 MHz, CDCl$_3$) δ 76.3, 74.7, 73.5, 67.6, 44.5, 41.0, 36.5, 30.7, 23.8, 18.2, 17.6, 16.8, 14.2

S14: FT-IR (on-bead KBr pellet) $v_{max}$: 3025, 2870, 1492, 1450, 1045, 883 cm$^{-1}$; gel phase $^{13}$C NMR (125 MHz, CDCl$_3$) δ 76.4, 73.5, 68.9, 44.8, 42.7, 41.0, 30.4, 23.8, 19.1, 18.3, 17.6, 16.8, 14.5

S15: FT-IR (on-bead KBr pellet) $v_{max}$: 3081, 2942, 1720, 1045, 884 cm$^{-1}$; gel phase $^{13}$C NMR (125 MHz, CDCl$_3$) δ 76.4, 75.0, 72.9, 67.3, 44.4, 41.0, 36.6, 32.2, 31.9, 30.9, 30.4, 26.0, 25.4, 25.1, 17.9, 17.6, 16.8, 14.3

S16: FT-IR (on-bead KBr pellet) $v_{max}$: 3023, 2922, 2362, 2335, 1029, 882 cm$^{-1}$; gel phase $^{13}$C NMR (125 MHz, CDCl$_3$) δ 155.9, 129.9, 121.7, 120.3, 74.7, 73.3, 67.7, 44.6, 41.1, 30.6, 18.1, 18.0, 17.6, 16.8, 14.5

S17: FT-IR (on-bead KBr pellet) $v_{max}$: 3058, 3025, 2930, 1160, 883 cm$^{-1}$; gel phase $^{13}$C NMR (125 MHz, CDCl$_3$) δ 73.7, 67.9, 62.0, 46.4, 44.8, 41.0, 30.7, 18.2, 17.8, 13.9

S18: FT-IR (on-bead KBr pellet) $v_{max}$: 3024, 2919, 1364, 1330, 1070, 883 cm$^{-1}$; gel phase $^{13}$C NMR (125 MHz, CDCl$_3$) δ 153.8, 137.3, 103.2, 73.8, 67.8, 64.9, 60.9, 56.4, 44.8, 41.0, 30.8, 18.1, 14.0

S19: FT-IR (on-bead KBr pellet) $v_{max}$: 3025, 2921, 1244, 1055, 883 cm$^{-1}$; gel phase $^{13}$C NMR (125 MHz, CDCl$_3$) δ 76.6, 76.4, 73.3, 67.4, 59.2, 44.5, 41.0, 30.4, 21.9, 18.2, 17.6, 16.8, 9.4

S20: FT-IR (on-bead KBr pellet) $v_{max}$: 3059, 3025, 2930, 1058, 883 cm$^{-1}$; gel phase $^{13}$C NMR (125 MHz, CDCl$_3$) δ 154.6, 149.6, 120.7, 114.9, 76.4, 74.6, 67.5, 56.0, 44.5, 41.0, 30.4, 18.0, 17.6, 16.8, 14.5

S21: FT-IR (on-bead KBr pellet) $v_{max}$: 3026, 2920, 2865, 1245, 1030, 883 cm$^{-1}$; gel phase $^{13}$C NMR (125 MHz, CDCl$_3$) δ 74.0, 67.8, 64.0, 60.9, 45.7, 44.8, 41.0, 30.7, 18.0, 14.3, 13.9

S22: FT-IR (on-bead KBr pellet) $v_{max}$: 3025, 2926, 1082, 883 cm$^{-1}$; gel phase $^{13}$C NMR (125 MHz, CDCl$_3$) δ 140.7, 132.8, 128.8, 127.9, 73.9, 67.6, 64.4, 44.8, 41.1, 30.8, 18.2, 18.1, 14.0

S23: FT-IR (on-bead KBr pellet) $v_{max}$: 3025, 2920, 1057, 883, 753 cm$^{-1}$; gel phase $^{13}$C NMR (125 MHz, CDCl$_3$) δ 76.4, 73.9, 73.3, 68.8, 58.2, 44.4, 41.1, 30.7, 30.4, 21.9, 21.8, 18.1, 17.6, 18.8, 14.3, 13.9

S24: FT-IR (on-bead KBr pellet) $v_{max}$: 3025, 2921, 1600, 1162, 883 cm$^{-1}$; gel phase $^{13}$C NMR (125 MHz, CDCl$_3$) δ 76.4, 73.3, 67.7, 44.5, 41.0, 30.9, 30.4, 17.9, 17.6, 16.8, 15.0, 14.3

S25: FT-IR (on-bead KBr pellet) $v_{max}$: 3024, 2922, 1259, 1035, 883 cm$^{-1}$; gel phase $^{13}$C NMR (125 MHz, CDCl$_3$) δ 154.7, 129.8, 126.4, 121.6, 74.9, 73.4, 67.7, 44.7, 41.1, 30.6, 18.0, 17.9, 17.6, 16.8, 14.5

S26: FT-IR (on-bead KBr pellet) $v_{max}$: 3459, 3025, 2938, 1169, 1035, 883 cm$^{-1}$; gel phase $^{13}$C NMR (125 MHz, CDCl$_3$) δ 73.6, 67.5, 47.2, 43.3, 40.9, 40.4, 30.8, 17.9, 14.3, 8.9

S27: FT-IR (on-bead KBr pellet) $v_{max}$: 3060, 2920, 2175, 1033, 884 cm$^{-1}$; gel phase $^{13}$C NMR (125 MHz, CDCl$_3$) δ 72.6, 66.9, 43.8, 40.4, 29.6, 17.7, 17.5, 13.0

Dimethyl-Cl (Si) FT-IR (on-bead KBr pellet) $v_{max}$: 3060, 2923, 1086, 698 cm$^{-1}$; gel phase $^{13}$C NMR (125 MHz, CDCl$_3$) δ 76.1, 70.5, 66.7, 43.5, 40.3, 29.3, 4.7.

Diethyl-Cl (S2) FT-IR (on-bead KBr pellet) $v_{max}$: 3060, 2911, 1042, 887, 591 cm$^{-1}$; gel phase $^{13}$C NMR (125 MHz, CDCl$_3$) δ 75.9, 72.7, 66.8, 43.7, 40.5, 29.8, 10.3, 6.5.

Diethyl-OMe (S40) FT-IR (on-bead KBr pellet) $v_{max}$: 3060, 2920, 2870, 1067, 883 cm$^{-1}$; gel phase $^{13}$C NMR (125 MHz, CDCl$_3$) δ 73.5, 67.6, 50.3, 44.4, 40.8, 30.4, 7.0, 6.0.

Diisopropylsilyl-OCH(CH$_2$Cl)$_2$ (541) FT-IR (on-bead KBr pellet) $v_{max}$: 3082, 2916, 1025, 881, 820 cm$^{-1}$; gel phase $^{13}$C NMR (125 MHz, CDCl$_3$) δ 72.5, 46.4, 41.1, 26.1, 18.0, 13.6, 13.4.

While certain embodiments of the present invention have been described and/or exemplified herein, it is contemplated that considerable variation and modification thereof are possible. Accordingly, the present invention is not limited to the particular embodiments described and/or exemplified herein.

PART A REFERENCES

1a. Newman, D. J.; Cragg, G. M. *J. Nat. Prod.* 2007, 70, 461.
2a. (a) Carlson, E. E. *ACS Chem. Biol* 2010, 5, 639. (b) Bottcher, T.; Pitscheider, M.; Sieber, S. A. *Angew. Chem. Int. Ed.* 2010, 49, 2680.
3a. (a) Månsson, M.; Phipps, R. K.; Gram, L.; Munro, M. H.; Larsen, T. O.; Nielsen, K. F. *J. Nat. Prod.* 2010, 73, 1126. (b) Araya, J. J.; Montenegro, G.; Mitscher, L. A.; Timmermann, B. N. *J. Nat. Prod.* 2010, 73, 1568.
4a. Watve, M. G.; Tickoo, R.; Jog, M. M.; Bhole, B. D. *Arch. Microbiol.* 2001, 176, 386.
5a. (a) Carlson, E. E.; Cravatt, B. F. Nat. Methods 2007, 4, 429. (b) Carlson, E. E.; Cravatt, B. F. *J. Am. Chem. Soc.* 2007, 129, 15780.
6a. Odendaal, A. Y.; Trader, D. J.; Carlson, E. E. Chem. Sci. 2011, 2, 760.
7a. Henkel, T.; Brunne, R. M.; Müller, H.; Reichel, F. *Angew. Chem. Int. Ed.* 1999, 38, 643.
8a. Hermanson, G. T. Bioconjugate Techniques; 2nd ed.; Elsevier Inc.: Rockford, Ill., 2008.
9a. Meloni, M. M.; White, P. D.; Armour, D.; Brown, R. C. D. *Tetrahedron* 2007, 63, 299.
10a. (a) Weinberg, J. M.; Gitto, S. P.; Wooley, K. L. *Macromolecules* 1998, 31, 15. (b) Wang, M.; Weinberg, J. M.; Wooley, K. L. *Macromolecules* 1998, 31, 7606. (c) Kocienski, P. J. Protecting Groups; Third ed.; Thieme: Stuttgart, 2005.
11a. Ojima, Y.; Yamaguchi, K.; Mizuno, N. *Adv. Synth. Catal.* 2009, 351, 1405.
12a. Liang, H.; Hu, L.; Corey, E. J. *Org. Lett.* 2011, 13, 4120
13a. Huczynski, A.; Stefanska, J.; Przybylski, P.; Brzezinski, B.; Bartl, F. *Bioorg. Med. Chem. Lett.* 2008, 18, 2585.
14a. (a) Mbah, G. C.; Speier, J. L. *J. Organomet. Chem.* 1984, 271, 77. (b) Chauhan, M.; Chauhan, B. P. S.; Boudjouk, P. *Org. Lett.* 2000, 2, 1027. (c) Huang, X.; Craita, C.; Awad, L.; Vogel, P. *Chem. Commun.* 2005, 1297.

PART B

Background and Summary

Natural products account for a significant proportion of modern day therapeutic agents. However, the discovery of novel compounds is hindered by the isolation process, which often relies upon extraction and chromatographic separation techniques. These methods, which are dependent upon the physicochemical properties of the compounds, have a limited ability to both purify and concentrate the minor components of a biological extract. Described herein is an isolation strategy based upon an orthogonal chemical feature, namely, functional group composition. Development of a functional group-targeted method is expected to achieve exceptional resolution given the large number of distinct moieties present in natural product extracts. The generation of controllably reversible covalent enrichment tags for the chemoselective isolation of alcohol-containing natural products from complex mixtures is described herein.

Natural products have long been recognized as privileged scaffolds due to their high propensity to interact with biological targets. [1] Thus, it is not surprising that naturally produced compounds and their derivatives are an essential component of today's pharmaceutical arsenal, with nearly half of the currently available drugs being of biological origin. [2] Natural products have also played myriad roles as chemical probes. [3, 4] The continued investigation of the small molecule repertoire of organisms such as plants and microbes is bound to prove fruitful for the discovery of new classes of bioactive compounds. Efforts to identify new leads, however, are often frustrated by the cumbersome and inefficient process of compound isolation.

Generally, natural products are identified by extraction of biological material (e.g., plant material, microbe pellet) and the crude extract is assayed for a desired activity. [5-7] Active extracts are then further purified, either by extraction and/or chromatographic methods. Although considerable advances have been made in separation technology yielding strategies that minimize solvent consumption and show increased resolving power, [8-10] purification of the active components of a crude extract, which often represent less than 1% by weight, is still considered a major bottleneck in natural products discovery.[6] Thus, the need to develop new isolation technologies is clear.

Current strategies facilitate enrichment based on a limited set of separation mechanisms that are dependent upon molecular properties such as solubility, charge state, or size. An alternative and complementary approach is to target functional group composition. In the early 1980s, Fréchet and coworkers demonstrated the capture of α,β-unsaturated lactone-containing allergens from natural oils with polymer-supported reagents. [11, 12] This approach, which targeted a very specific functionality, has not been significantly utilized because a practical natural products discovery toolkit requires the development of strategies to address more prevalent functional groups such as amines, carboxylic acids and alcohols using highly selective and readily reversible reaction conditions.

Development of a functional group-targeted method for selective enrichment and profiling of metabolites for metabolomic studies was recently described. [13, 14; the disclosure of the foregoing is incorporated herein in its entirety by reference. In addition, the entirety of the disclosure of each of the publications cited herein is also incorporated herein by reference.] The devised methods facilitate exploration of the amine, thiol, carboxylic acid and ketone/aldehyde complements of a cell. In the described metabolomic studies, a permanent tagging strategy was utilized in which the metabolites were covalently altered with a tag that subsequently aids in their detection by mass spectrometry. It is believed that a permanent tag would be detrimental to natural products discovery efforts because of its unpredictable effect on biological activity. A tagging strategy that employs reactions that are controllably reversible to enable covalent capture of small molecules, facilitating their chemoselective enrichment, followed by release of the unaltered chemical structures is described herein. With this approach, targeted compounds, including low-abundance molecules, can be enriched independently of their physicochemical properties.

The agents described herein, referred to as reversible enrichment tags, are immobilized on solid support to enable the selective isolation of fractions of natural products present in a complex biological matrix. Following capture (i.e. formation of a bond with the reversible enrichment tag), elimination of compounds that do not contain the targeted functional group is accomplished by washing of the resin. Enriched compounds are liberated from the resin using gentle conditions that are expected not to interfere with either the structural integrity of the natural products or subsequent bioassays. Described herein is the development of a reversible enrichment tag for the capture of alcohol-containing natural products.

A functional group-targeted enrichment strategy includes several considerations. First, the capture reaction between the molecules to be enriched and the reversible enrichment tags should be chemoselective for the functional group. The devised reagent reversible enrichment tags should also facilitate the immobilization of a range of alcohols (e.g., primary, secondary). Additionally, the covalent bond formed between the natural products and the reversible enrichment tags attached to the solid support should be sufficiently stable to withstand extensive washing protocols to remove all compounds not containing the targeted functionality (e.g. alcohols). However, the formed bond should be readily cleavable to permit release of the enriched compounds. As mentioned, the conditions for immobilization and release should be gentle; however, the reagents utilized and their resulting byproducts should also enable direct structural and functional characterization of the isolated compounds. In one aspect of the methods described herein, volatile reagents are employed and volatile byproducts are generated during the course of the reactions minimizing the need for additional purification after release of the enriched compounds.

DETAILED DESCRIPTION

Several illustrative embodiments of the invention are described by the following enumerated clauses:

101. A polymeric reagent for use in the selective enrichment of hydroxyl-group-containing compounds from a mixture:

comprising a polymer having one or more functional groups of formula $(CH_2)_n$—O—$Si(R^1)(R^2)X$ covalently attached to the polymer wherein the functional group is capable of reacting with the hydroxyl group-containing compounds when the mixture containing the compounds contacts the reagent;

n is 1 to 4;

$R^1$ and $R^2$ are independently selected in each instance from the group consisting of $C_1$-$C_8$ alkyl and $C_3$-$C_8$ cycloalkyl; and X is selected from the group consisting of Cl, Br, and $OS(O)_2CF_3$.

102. The polymeric reagent of clause 101, wherein the functional group is attached to a main chain or side chain of the polymer by a linking group.

103. The polymeric reagent of clause 101 or 102 wherein the linking group is a phenylene group.

104. The polymeric reagent of any one of clauses 101 to 103 wherein the linking group is a para-phenylene group.

105. The polymeric reagent of any one of clauses 101 to 104 wherein $R^1$ and $R^2$ are $C_1$-$C_8$ alkyl.

106. The polymeric reagent of any one of clauses 101 to 105 wherein n is 1.

107. The polymeric reagent of any one of clauses 101 to 106 wherein the polymer is a polyolefin, polyamide, polyurethane, or polycarbonate.

108. The polymeric reagent of any one of clauses 101 to 107 wherein the polymer is a polyolefin.

109. The polymeric reagent of any one of clauses 101 to 108 wherein the polymer is a polystyrene.

110. The polymeric reagent of any one of clauses 101 to 109 wherein polymeric reagent is a polystyrene of formula

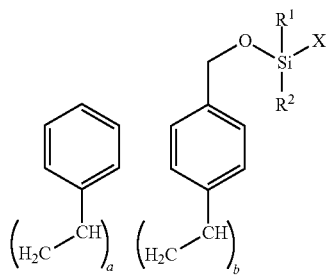

wherein the ratio of b to a is from 1:99 to 1:1, and wherein the polystyrene is crosslinked with from 0.5 to 10.0% divinylbenzene.

111. The polymeric reagent of any one of clauses 101 to 110 wherein the functional group is $CH_2OSi(CH_3)_2Cl$ or $CH_2OSi(CH_2CH_3)_2Cl$.

112. A process for preparing a second mixture selectively enriched in hydroxyl group containing compounds from a first mixture containing the hydroxyl group-containing compounds, the method comprising the step of
(a) contacting the first mixture with a polymeric reagent of any one of clauses 1 to 12;
wherein one or more of the functional groups forms a covalent bond with the hydroxyl group of one or more of the hydroxyl group-containing compounds.

113. The process of clause 112 further comprising the step (b) of washing the polymer resulting from step (a) with a solvent selected from the group consisting of optionally branched $C_5$-$C_{10}$ alkanes, optionally-branched $C_1$-$C_5$ alcohols, benzene, toluene, xylenes, $C_1$-$C_5$ alkyl $C_2$-$C_5$ alkanoates, where each of the alkyl or the alkanoate is optionally branched, $C_1$-$C_4$ alkylnitriles, DMF, THF, dioxane, DMSO, $C_1$-$C_4$ haloalkanes, and combinations thereof.

114. The process of clause 112 or 113 further comprising the step (c) of cleaving the covalent bond between the functional group and the hydroxyl group-containing compound.

115. The process of any one of clauses 112 to 114 wherein the first mixture is an extract of plant material or an extract of a fermentation broth.

116. A process for preparing a third mixture selectively enriched in aliphatic hydroxyl group containing compounds and a second mixture selectively enriched in aromatic hydroxyl group containing compound from a first mixture containing the aliphatic and aromatic hydroxyl group-containing compounds, the method comprising the steps of:
(a) contacting the first mixture with the polymeric reagent of any one of clauses 101 to 111 wherein one or more of the functional groups forms a covalent bond with the hydroxyl group of one or more of the hydroxyl group-containing compounds;
(b) washing the polymer resulting from step (a) with a solvent selected from the group consisting of optionally branched $C_5$-$C_{10}$ alkanes, optionally-branched $C_1$-$C_5$ alcohols, benzene, toluene, xylenes, $C_1$-$C_5$ alkyl $C_2$-$C_5$ alkanoates, where each of the alkyl or the alkanoate is optionally branched, $C_1$-$C_4$ alkylnitriles, DMF, THF, dioxane, DMSO, $C_1$-$C_4$ haloalkanes, and combinations thereof;
(c) selectively cleaving the covalent bond between the functional group and the aromatic hydroxyl group containing compounds;
(d) washing the polymer resulting from step (c) with a solvent selected from the group consisting of optionally branched $C_5$-$C_{10}$ alkanes, optionally-branched $C_1$-$C_5$ alcohols, benzene, toluene, xylenes, $C_1$-$C_5$ alkyl $C_2$-$C_5$ alkanoates, where each of the alkyl or the alkanoate is optionally branched, $C_1$-$C_4$ alkylnitriles, DMF, THF, dioxane, DMSO, $C_1$-$C_4$ haloalkanes, and combinations thereof to yield the second mixture; and
(e) cleaving the covalent bond between the functional group and the aliphatic hydroxyl group-containing compound.

117. The process of clause 116 wherein the selective cleavage of step (c) comprises contacting the polymeric reagent from step (b) with a mixture of 1,1,3,3-tetramethylguanidine and acetic acid.

Many natural products are rich in oxygen atoms, often found as alcohols or in heterocycles. [15, 16] The enrichment of alcohol-containing natural products, using a reversible tagging strategy using a silyl-functionalized solid support is described herein (Scheme 101). Immobilization of alcohol-containing compounds is accomplished by activation of the resin to generate a resin-bound silyl triflate or chloride, followed by addition of the alcohol and tertiary amine (e.g. triethylamine). After extensive washing, release is performed using HF-pyridine followed by quenching with TMSOMe. Although some functionalities, such as the epoxide functionality, may be sensitive to HF-pyridine, it was found herein that this reagent provides the best overall cleavage efficiency. Alternative conditions were less general requiring long reaction times, elevated reaction temperatures, and/or subsequent purification steps.

Scheme 101 General strategy for enrichment of alcohol-containing natural products.

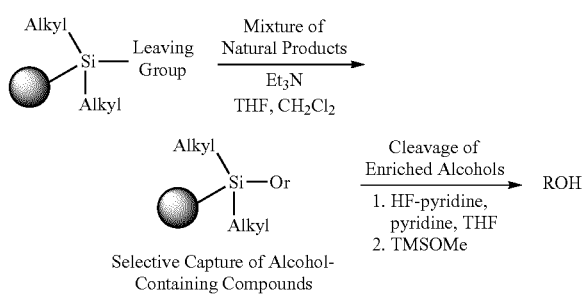

Although silyl-functionalized resins have been extensively explored for use in synthetic chemistry, [17-21] their application to complex mixtures of compounds is not widely reported. Described herein are solid supports with reversible enrichment tags attached that can efficiently and chemoselectively capture a broad range of alcohols.

TABLE 101
Yields of enrichment for alcohol-, amine-, carboxylic acid- or thiol-containing small molecule standards with capture resins. Enrichment was quantified by LC-MS.
| Structure | # | Yield |
|---|---|---|
| 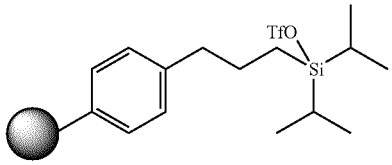 [SMILES: Cc1ccc(CCC[Si](OS(=O)(=O)C(F)(F)F)(C(C)C)C(C)C)cc1] | 101 | |
| 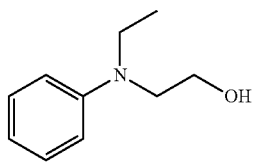 | S6 | 70% |
| FmocNH~~~OH | 17 | 63% |
| 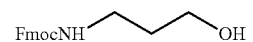 | 106 | 60% |
| 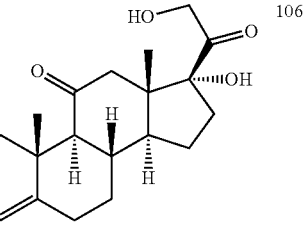 | 107 | 90% |
| 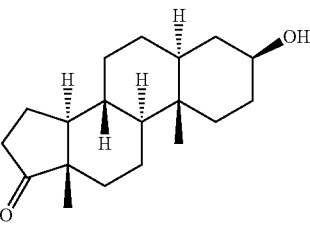 | 108 | 83% |
| 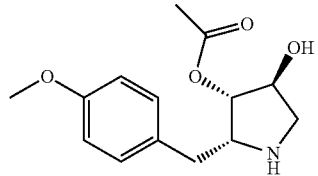 [SMILES: COc1ccc(C[C@H]2NC[C@H](O)[C@H]2OC(C)=O)cc1] | 109 | 68% |
| 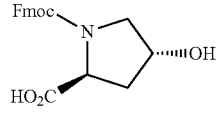 | | 68% |

TABLE 101-continued
Yields of enrichment for alcohol-, amine-, carboxylic acid- or thiol-containing small molecule standards with capture resins. Enrichment was quantified by LC-MS.
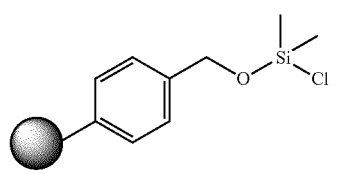
110
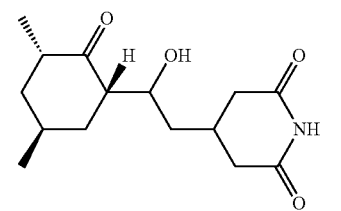 [SMILES: C[C@@H]1C[C@@H](C(O)CC2CC(=O)NC(=O)C2)C(=O)[C@@H](C)C1]
10
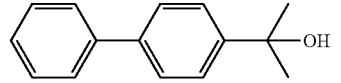
111    0%
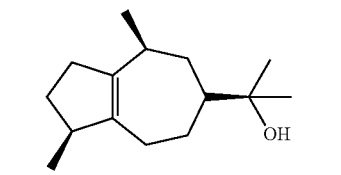
112    0%
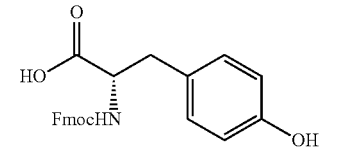
113    67%
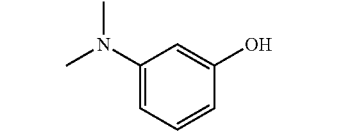
18    53%
Compounds to Assess Chemoselectivity
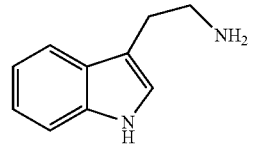 [SMILES: NCCc1c[nH]c2ccccc12]
S7    3%
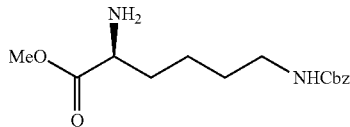 [SMILES: COC(=O)[C@@H](N)CCCCNC(=O)OCc1ccccc1]
19    45%
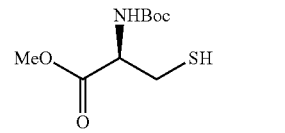
20    46%

TABLE 101-continued

Yields of enrichment for alcohol-, amine-, carboxylic acid- or thiol-containing small molecule standards with capture resins. Enrichment was quantified by LC-MS.

| | | |
|---|---|---|
| (structure of S4: Fmoc-Val-OH) | S4 | 38% |
| (structure of S5: pyrrolidine diol with p-methoxybenzyl and acetate) | S5 | 96% |

| 102 (benzyl-O-Si(Me)₂-Cl resin) | 103 (benzyl-O-Si(Et)₂-Cl resin) |
|---|---|
| 0% | 14% |
| 87% | 68% |
| 0% | 62% |
| 81% | 92% |
| 28% | 66% |
| 97% | 91% |
| 89% | 29% |
| 0% | 0% |
| 53% | 0% |
| 66% | 79% |
| 27% | 21% |
| Compounds to Assess Chemoselectivity | |
| 0% | 0% |
| 0% | 0% |
| 0% | 0% |
| 0% | 0% |
| 0% | 0% |

Use of a Silyl-Functionalized Resin

Initial studies examined the utility of a commercially available solid support, (4-methoxyphenyl) diisopropylsilylpropyl polystyrene resin, which is activated as the triflate just prior to use (Table 101, 101). [17] Described herein is the capture several alcohol standards, followed by resin washing, release and quantification by liquid chromatography-mass spectrometry (LC-MS) analysis. Eleven standards with varying physicochemical properties and alcohol accessibility (Table 101, S6, 17, 106-113, and 18) were subjected to the activated resin (0.1 equiv each compared to resin, capture performed as mixtures of 3-4 compounds). Enrichment yields were dependent upon the steric accessibility of the alcohol. For example, enrichment of most primary and secondary alcohol- and phenol-containing compounds proceeded well (S6, 17, 106-110, 113 and 18; yields indicate the amount of compound detected following immobilization and release). However, tertiary alcohols (111 and 112) were not enriched by resin 101.

The chemoselectivity of resin 101 was further measured by subjecting amine-, thiol- and carboxylic acid-containing compounds (S7, 19, 20, S4, and S5) to the enrichment protocol. All three of these functional group classes were captured in moderate to high yields suggesting the need for resins with higher chemoselectivity.

Generation of Chemoselective Enrichment Reagents

Synthesis and evaluation of a library of resins with varying linkers and silyl substitution patterns revealed that a benzyl alcohol-derived siloxyl resin afforded the required chemoselectivity (Table 101, resins 102 and 103; resins found to be non-selective not shown). In addition to alcohol selectivity, these siloxyl-functionalized resins have several other advantages over the silyl-functionalized resin 101. First, synthesis of the activated resins is accomplished in one step from hydroxymethyl polystyrene resin (Scheme 102). As a result, each analog is easy to produce. In general, synthesis of silane-functionalized resins requires multiple steps rendering the construction of analogs more labor intensive.

A further benefit of the siloxyl-functionalized resins is their ability to be regenerated (Scheme 102). Upon cleavage of enriched alcohols from these solid supports, the starting resin is reproduced, whereas cleavage of silane-functionalized resins yields an unrecoverable silylfluoride product. Evidence of this advantage is shown the observation that the loading capacities of resins 102 and 103 do not change after subjecting them to a round of alcohol capture and release followed by reactivation (Table 102). Examination of the total ion chromatograms of enriched compounds also illustrated the high level of purity provided by this strategy.

Scheme 102 Synthesis and regeneration of benzyl alcohol-derived resins.

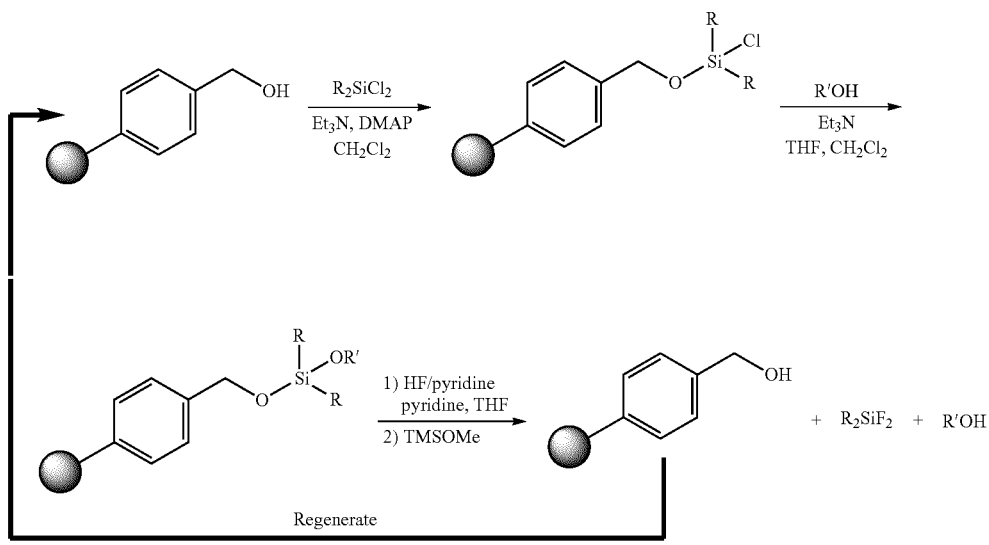

Hydroxylmethyl polystyrene resin can be functionalized with a variety of dichlorodialkyl silanes yielding the capture reagents. Following alcohol enrichment and cleavage, the starting resin is regenerated as indicated by the arrow.

Comparison of the dimethyl- and diethyl-substituted resins (102 and 103, respectively) demonstrated that resin 103 provides increased overall enrichment efficiency. In particular, the less sterically demanding resin 102 shows lower yields for less hindered alcohols as these compounds suffer from premature cleavage off of the resin during the washing protocol (e.g., compounds S6, 106, 108). Additionally, the less hindered resin 102 is more reactive than resin 103, increasing its susceptibility to hydrolysis and/or inconsistent enrichment yields (data not shown). Interestingly, resin 102 promotes recovery of a tertiary alcohol (12) suggesting that this resin may be useful for the isolation of extremely hindered alcohols.

Also described herein methods that enable separation of compounds bearing aliphatic and aromatic (e.g. phenolic) hydroxyls. A chemoselective polystyrene-based resin is used to capture compounds containing both classes of molecules; and then a selective release strategy is employed, as shown in Scheme 103. The phenol-containing molecules are released by contacting the resin containing the captured compounds with a mixture comprising 1,1,3,3-tetramethylguanidine (TMG), glacial acetic acid, acetonitrile (ACN), and tetrahydrofuran (THF). This cleavage cocktail results in release of only molecules that contain an aromatic hydroxyl functional group from the resin, Scheme 103. The aliphatic hydroxyl molecules are subsequently released, as described herein using HF/pyridine.

Scheme 103. Chemoselective release of aryl hydroxyl containing molecules, followed by isolation of those molecules that contain an aliphatic hydroxyl moiety.

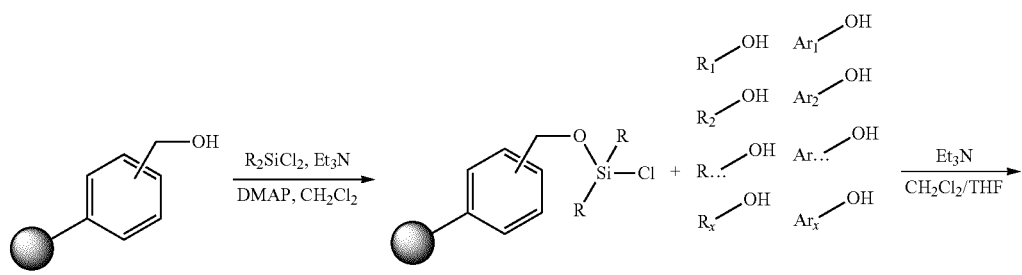

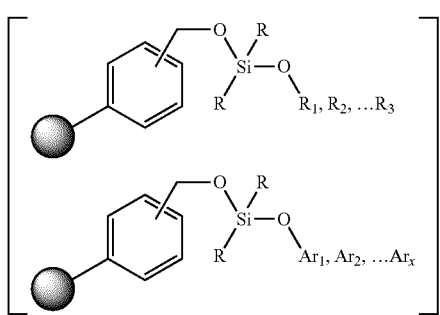 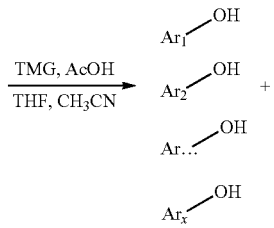 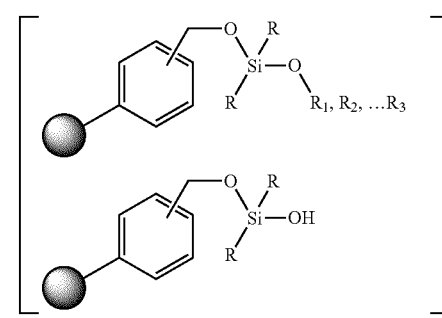
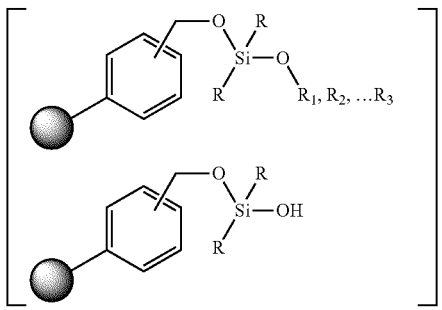 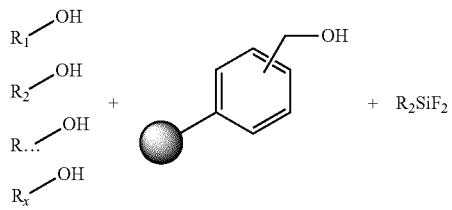

It is believed that this selective cleavage protocol will allow access to molecules that have previously gone undetected in complex mixtures of compounds (e.g. during isolation of naturally occurring compounds). The utility of this method is shown in Tables 104 and 105, which demonstrate the chemoselectivity of the capture step and the excellent to moderate yields for the capture and release of standards.

Also described herein are reaction conditions and reagents useful for cleavage of Si—O bonds under neutral cleavage conditions. It is appreciated that these conditions and reagents may be valuable in solution phase deprotection strategies during synthesis of complex molecules.

Enrichment of an Endogenous Natural Product

In one embodiment, the utility of this strategy used in a complex extract, i.e. the enrichment of an endogenously produced natural product, anisomycin (108), is described. This compound is produced by *Streptomyces griseolus* [22] and is a known inhibitor of protein biosynthesis.[23] An extract of this organism was subjected to the capture strategy (resin 103) resulting in the obtaining the natural product with a similar yield to that observed upon capture of the pure standard [82% recovery (31 nmol) compared to 66% with standard.

In another embodiment, the alcohol enrichment capabilities and chemoselectivity of this strategy in the context of an extract are demonstrated for a mixture containing two alcohol-containing compounds (106 and 107) and one each of an amine-, thiol-, and carboxylic acid-containing standard (S7, 20, S4) prior to capture. Both alcohols were detected in the cleavage solution, demonstrating of the utility of resin 103 for alcohol isolation. The amine-, thiol-, and carboxylic acid-containing compounds were not enriched from the extract validating the initial chemoselectivity results.

In another aspect, the ratio of enrichment is calculated to further illustrate that alcohol-containing compounds are enriched compared to molecules containing other functional groups. Following the capture and release protocol, at least a 24-fold enrichment of the alcohols was seen in comparison to compounds not containing this functionality in all cases (Table 103). Extract material was also subjected to deactivated resin to confirm that the observed alcohol enrichment was a result of capture by the activated silane and not due to non-specific binding to the resin.

Facile identification of new natural products will require the development of novel isolation strategies. Described herein is a functional group-targeted approach, providing an example of a chemoselective method for enrichment of alcohol-containing compounds. In addition to natural products exploration, it is believed that the described reagents are useful in diverse applications such as chemoselective synthetic scavenging and isolation reagents and metabolomic profiling.

In another embodiment, the compounds described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

METHODS AND EXAMPLES

General Information

Resin reactions were performed in fritted vessels (Biospin vessels from Biorad) under an inert atmosphere of Ar or $N_2$. Resins were purchased from EMD Biosciences. All other chemicals were purchased from VWR or Sigma-Aldrich and used without further purification. Solvents were purchased as anhydrous and not further purified. Triethylamine was distilled over barium oxide.

Sample analysis was performed on an Agilent 1200 LC-MS-TOF equipped with a reverse phase column (ZORBAX Eclipse Plus C18, Rapid Resolution HT, 1.8 micron, 2.1×50 mm). All sample and standard curve analysis was performed with the following gradient: isocratic elution of 100% A at 0.5 mL/min for 2 min followed by a linear gradient of 0-100% B at 0.5 mL/min over 6 min, then an isocratic elution for 2 min at 100% B, and re-equilibration with 100% A for 4 min (A: 95:5 $H_2O$:$CH_3CN$, 0.1% ammonium acetate; B 95:5 $CH_3CN$: $H_2O$, 0.1% ammonium acetate). Fragmentation voltages ranged from 75V to 175V. Gel-phase [13] C nuclear magnetic resonance (NMR) spectra [20] were recorded on a Varian 1500 or a Varian VXR-400 instrument. Chemical shifts are reported relative to residual solvent peaks in parts per million. Infrared (IR) spectra were recorded using a Perkin Elmer Spectrum One FT-IR as a KBr pellet.

(4-Methoxyphenyl)Diisopropylsilylpropyl Polystyrene Resin Activation

A 10 mL fritted polypropylene column was charged with 126 mg (0.176 mmol) of (4-methoxyphenyl)diisopropylsilylpropyl polystyrene resin (loading capacity of 1.4 mmol/g) and equipped with a rubber septum. The resin was flushed with $N_2$ for 10 min. A solution of 94.0 μL trifluoroacetic acid (1.06 mmol, 6.0 equiv relative to resin) and 2.3 mL anhydrous $CH_2Cl_2$ was added to the resin. The resin turned red and was agitated at room temperature for 30 min. After activation, the resin was washed with 2 mL anhydrous $CH_2Cl_2$ three times and aliquoted into four 2 mL oven dried vials using 1.2 mL of anhydrous $CH_2Cl_2$. The vials were capped and placed under $N_2$. Resin was utilized immediately in coupling reactions.

Benzylsiloxane Resin (102 and 103) Synthesis

A 20 mL scintillation vial was charged with 200 mg (0.22 mmol) of hydroxymethyl polystyrene resin (loading capacity of 1.1 mmol/g) and equipped with a rubber septum. After flushing the resin with $N_2$ for 10 min, the vial was charged with 4 mL anhydrous $CH_2Cl_2$ and the resin was allowed to swell for 5 min. To the swollen resin was added 430 μL (3.1 mmol, 14 equiv relative to Si) of freshly distilled triethylamine, 330 μL (2.2 mmol, 10 equiv relative to Si) of dichlorodiethylsilane or 300 μL dichlorodimethylsilane (2.2 mmol, 10 equiv relative to Si) and 32 mg (0.26 mmol, 1.2 equiv relative to Si) of 4-dimethylaminopyridine. The vial was capped and the reaction was agitated for 4 h at room temperature. The resin was filtered over a 10 mL fritted polypropylene column and washed with 2×10 mL anhydrous $CH_2Cl_2$ and aliquoted into four 5 mL oven dried vials using 2 mL of anhydrous $CH_2Cl_2$. Three aliquoted vials were capped and placed under $N_2$ for subsequent coupling reactions, the fourth vial was transferred back to a biospin vial and rinsed three times with 1:1 THF:MeOH to hydrolyze the chlorine and yield deactivated resin to act as a control. Resin was used within 10 min of generation to prevent excessive hydrolysis. Dimethylchlorobenzylsiloxane resin (102): FT-IR (on-bead KBr pellet) $v_{max}$: 3059, 1601, 1260, 1017, 909, 733, 538 $cm^{-1}$; gel-phase $^{13}C$ NMR (125 MHz, $CDCl_3$) δ: 53.3, 40.3, 2.2. Diethylchlorobenzylsiloxane resin (103): FT-IR (on-bead KBr pellet) $v_{max}$: 3060, 1601, 1017, 909, 734, 539 $cm^{-1}$; gel-phase $^{13}C$ NMR (125 MHz, $CDCl_3$) δ: 53.3, 40.3, 8.3, 6.2.

Determination of Resin Loading Capacity.

For each of the resins, 200 mg was placed in a dry 20 mL scintillation vial. The resin was swollen with 4 mL of anhydrous $CH_2Cl_2$ under Ar. Next, 14 equiv of triethylamine relative to the initial loading capacity of the resin was added, followed by 10 equiv of the dichlorodialkylsilane. 4-Dimethylaminopyridine (1.1 equiv) was added and the vial was capped and allowed to agitate at room temperature for 4 h. The resin was transferred to a 10 mL biospin vial and rinsed under Ar with anhydrous $CH_2Cl_2$ (2×2 mL). Next, 3 mL of anhydrous $CH_2Cl_2$ was added to the resin and allowed to swell for 1 min. The resin was aliquoted into five 2 mL vials (40 mg of resin into each). One aliquot acted as a control, which was hydrolyzed as described previously in the manuscript Experimental section. To each of the vials was added 8.0 equiv of triethylamine and 3.0 equiv of Fmoc-aminopropanol dissolved in 1 mL of anhydrous THF. The reactions were agitated overnight at room temperature. Resin was transferred to a 2 mL biospin vessel and subjected to the standard wash protocol. The resins were dried overnight at room temperature in a vacuum desiccator at 30 mmHg. Coupled resin was transferred to polypropylene vials (5 mL). To the resin was added 500/50/50 μL (v/v) of a freshly prepared solution of THF/HF.pyridine (70/30 wt %)/pyridine (1.6 mmol of HF, 28 equiv relative to Si) and the reaction was gently agitated at room temperature for 3 h. To this was added 500 μL of TMSOMe (3.6 mmol, 83 equiv relative to Si) to quench excess HF and the resin was agitated for an additional 30 min at room temperature. The resin was washed with THF (3×1 mL×10 minutes) and filtered over a 1 mL fritted polypropylene column into a 20 mL scintillation vial. The THF wash was concentrated under reduced pressure with no additional heating and the sample was redissolved in 10 mL of 2:1:1 H2O/THF/MeOH. Analysis was performed by injection of 1 μL of this solution onto a LC-MS-TOF and comparing the observed peak area to that of standard curve data. The average of the three replicates was used as the loading capacity for all subsequent coupling experiments. Dimethylbenzyl siloxane resin loading capacity 0.15 mmol/g; diethylbenzyl siloxane resin loading capacity 0.18 mmol/g (Table 102).

TABLE 102

Loading capacities of synthesized resins.

| | First Capture Loading Capacity | Second Capture Loading Capacity |
|---|---|---|
| Dimethylbenzyl siloxane resin 102 a | 0.15 mmol/g | 0.16 mmol/g |
| Dimethylbenzyl siloxane resin 102 b | 0.16 mmol/g | 0.12 mmol/g |
| Dimethylbenzyl siloxane resin 102 c | 0.14 mmol/g | 0.13 mmol/g |
| Dimethylbenzyl siloxane resin 102 Average | 0.15 mmol/g | 0.14 mmol/g |
| Diethylbenzyl siloxane resin 103 | 0.19 mmol/g | 0.23 mmol/g |
| Diethylbenzyl siloxane resin 103 | 0.18 mmol/g | 0.19 mmol/g |
| Diethylbenzyl siloxane resin 103 | 0.17 mmol/g | 0.21 mmol/g |
| Diethylbenzyl siloxane resin 103 Average | 0.18 mmol/g | 0.21 mmol/g |

Capture of Alcohols onto Resin

To activated resin was added 50 μL of freshly distilled triethylamine (0.35 mmol, 8.0 equiv relative to Si). A stock solution of model alcohols was prepared in 500 μL of anhydrous THF, which contained three or four compounds. From this solution, 100 μL was added to each reaction vessel (0.1 equiv of each alcohol relative to resin loading capacity). The coupling reactions were gently agitated at room temperature overnight (~16 h). The resin was transferred to a 2 mL fritted polypropylene column and subjected to the wash protocol described in the Supplementary Information. Resins were dried overnight at room temperature in a vacuum desiccator at 30 mmHg.

Resin Wash Protocol

Resin is transferred to a fritted vessel and rinsed as follows: $CH_2Cl_2$ (suspend resin in 2 mL for 10 min, rinse 2×2 mL), THF (suspend resin in 2 mL for 10 min, rinse 2×2 mL), DMSO/$CH_2Cl_2$ (1:1, suspend resin in 2 mL for 10 min, rinse 2×2 mL), THF (suspend resin in 2 mL for 10 min, rinse 2×2 mL), DMSO/$CH_2Cl_2$ (1:1, suspend resin in 2 mL for 10 min, rinse 2×2 mL), $CH_2Cl_2$ (suspend resin in 2 mL for 10 min, rinse 2×2 mL), toluene (suspend resin in 2 mL for 5 min, rinse 2×2 mL), DMF (suspend resin in 2 mL for 5 min, rinse 2×2 mL), $CH_2Cl_2$ (suspend resin in 2 mL for 5 min, rinse 2×2 mL), hexanes (suspend resin in 2 mL for 5 min, rinse 2×2 mL), $CH_2Cl_2$/MeOH (3:1, suspend resin in 2 mL for 5 min, rinse 2×2 mL), CHCl₃ (3×2 mL; ensure that solvent has not become acidic to minimize premature cleavage of the resin could result), CH₂Cl₂ (3×2 mL).

Release of Alcohols from Resin

Coupled resin was transferred to polypropylene vials. To the resin was added 500/50/50 µL (v/v) of a freshly prepared solution of THF/HF.pyridine (70/30 wt %)/pyridine (2.0 mmol of HF, 45 equiv relative to Si) and the reaction was gently agitated at room temperature for 3 h. To this was added 500 µL of TMSOMe (3.6 mmol, 83 equiv relative to Si) to quench excess HF and the resin was agitated for an additional 30 min at room temperature. The resin was washed with THF (3×1 mL×10 min) and filtered over a 1 mL fritted polypropylene column into a 20 mL scintillation vial. The THF wash was concentrated under reduced pressure with no heating and the sample was dissolved in 5 mL of 2:1:1 H₂O/THF/MeOH. Analysis was performed by injection of 1 µL of this solution onto a LC-MS-TOF and comparing the observed peak area to that of standard curve data.

Ratios of Enrichment of Captured Compounds Compared to Non-Captured Compounds.

To illustrate that the alcohol-containing compounds are being dramatically enriched in comparison to the molecules containing other functional groups, the ratio of enrichment is calculated. The ratio of each alcohol to the chemoselective set of compounds was calculated and normalized. Normalization is required given that although an equivalent number of moles of each compound was used, the ionization efficiency of each compound is unique, making the observed peak areas dramatically different. Accordingly, the initial ratios were normalized to a 1:1 ratio and this factor was applied to the post-capture data. In all cases, following the capture and release protocol at least a 24-fold enrichment of the alcohols was seen in comparison to the non-alcohol compounds.

TABLE 103

|  | Peak Ratio Before Capture | Normalization Factor | Peak Ratio After Capture | Normalized Ratio After Capture |
|---|---|---|---|---|
| Androsterone/Fmoc-Val-OH | 0.1097 | 9.1165 | 3.5064 | 31.9657 |
| Androsterone/Trypamine | 0.1298 | 7.7039 | 46.6193 | 359.1488 |
| Androsterone/Cys-methyl ester | 0.6922 | 1.4447 | 16.6610 | 24.0698 |
| Cortisone/Fmoc-Val-OH | 0.1560 | 6.4117 | 5.3185 | 34.1004 |
| Cortisone/Trypamine | 0.1846 | 5.4182 | 70.7123 | 383.1332 |
| Cortisone/Cys-methyl ester | 0.9842 | 1.0161 | 25.2715 | 25.6772 |

Separation of Aliphatic-Hydroxyl Containing Compounds from Aromatic-Hydroxyl Containing Compounds.

Hydroxyl-containing molecules are subjected to the capture conditions described in this application. The resin (40 mg scale) was rinsed following the described protocol, was transferred to a 2 mL eppendorf tube and swollen with 400 µL of THF. In a separate vial the following were mixed together: 25 µL of TMG (0.2 mmol, 20 equiv), 12 µL of glacial acetic acid (0.24 mmol, 1.14 equiv) and 100 µL of acetonitrile. This mixture was added to the resin and agitated for 15 min at 30° C. The resin was transferred to a 2 mL biospin vessel and rinsed with THF, DCM, and THF. All organic washes are combined and concentrated to dryness to yield the phenol mixture. The resin was transferred back to a 2 mL eppendorf tube and subjected to the previously described HF/pyr/pyr cleavage conditions to yield the aliphatic hydroxyl-containing molecules.

TABLE 104

Recovery yields of model compounds utilizing the TMG and acetic acid method with a variety of resin derivatives.

| Model Compound | R = Me R' = Me | R = Et R' = Me | R = Cyclohexyl R' = Methyl | R = Decyl R' = Methyl | R = Isobutyl R' = Methyl | R = n-Butyl R' = Methyl |
|---|---|---|---|---|---|---|
| 4-acetamidophenol | 60% | 52% | 22% | 71% | 40% | 58% |
| 2-acetamidophenol | 35% | 53% | 75% | 67% | 62% | 66% |
| 3-acetamidophenol | 60% | 65% | 10% | 58% | 54% | 48% |

TABLE 104-continued

Recovery yields of model compounds utilizing the TMG and acetic acid method with a variety of resin derivatives.

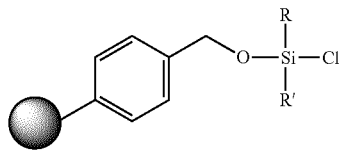

| Model Compound | R = Me<br>R' = Me | R = Et<br>R' = Me | R = Cyclohexyl<br>R' = Methyl | R = Decyl<br>R' = Methyl | R = Isobutyl<br>R' = Methyl | R = n-Butyl<br>R' = Methyl |
|---|---|---|---|---|---|---|
| 3-(diethylamino)phenol | 71% | 30% | 8% | 50% | 25% | 42% |
| 3-(dimethylamino)phenol | 73% | 46% | 41% | 55% | 29% | 45% |
| 4-(4-hydroxyphenyl)-2-butanone | 52% | 48% | 15% | 49% | 42% | 18% |
| 2-amino-4-tert-amylphenol | 53% | 21% | 12% | 30% | 33% | 28% |
| epiandrosterone | 18% | 4% | 1% | 4% | 2% | 5% |
| CBz-NH-(CH2)4-OH | 23% | 7% | 2% | 13% | 7% | 13% |
| diisopropanolamine | 14% | 4% | 5% | 6% | 9% | 1% |
| atropine | 22% | 1% | 3% | 19% | 10% | 17% |

TABLE 104-continued

Recovery yields of model compounds utilizing the TMG and acetic acid method with a variety of resin derivatives.

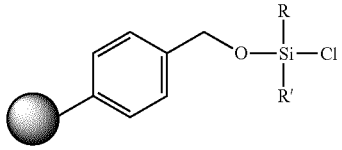

| Model Compound | R = Me<br>R' = Me | R = Et<br>R' = Me | R = Cyclohexyl<br>R' = Methyl | R = Decyl<br>R' = Methyl | R = Isobutyl<br>R' = Methyl | R = n-Butyl<br>R' = Methyl |
|---|---|---|---|---|---|---|
| 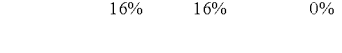 | 16% | 16% | 0% | 3% | 2% | 2% |
|  | 25% | 12% | 8% | 2% | 2% | 0% |
|  | 10% | 25% | 2% | 11% | 8% | 11% |

TABLE 105

Recovery yields of model compounds using a mixture of HF/pyr/pyr after the resin had previously been subjected to a mixture of TMG/acetic acid to cleave phenols.

| Model Compound | R = Me<br>R' = Me | R = Et1<br>R' = Me | R = Cyclohexyl<br>R' = Methyl | R = Decyl<br>R' = Methyl | R = Isobutyl<br>R' = Methyl | R = n-Butyl<br>R' = Methyl |
|---|---|---|---|---|---|---|
|  | 2% | 13% | 51% | 9% | 24% | 13% |
|  | 0% | 1% | 0% | 0% | 0% | 0% |

TABLE 105-continued

Recovery yields of model compounds using a mixture of HF/pyr/pyr after the resin
had previously been subjected to a mixture of TMG/acetic acid to cleave phenols.

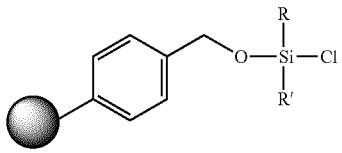

| Model Compound | R = Me<br>R' = Me | R = Et1<br>R' = Me | R = Cyclohexyl<br>R' = Methyl | R = Decyl<br>R' = Methyl | R = Isobutyl<br>R' = Methyl | R = n-Butyl<br>R' = Methyl |
|---|---|---|---|---|---|---|
| 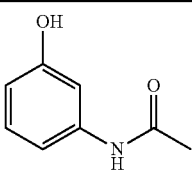 | 1% | 2% | 56% | 43% | 42% | 32% |
| 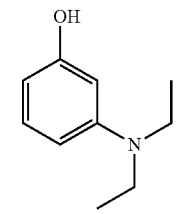 | 7% | 28% | 59% | 36% | 33% | 32% |
| 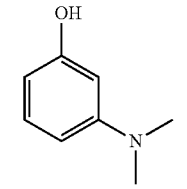 | 4% | 20% | 51% | 20% | 23% | 22% |
| 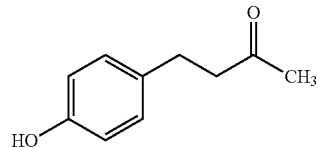 | 2% | 4% | 42% | 6% | 30% | 16% |
| 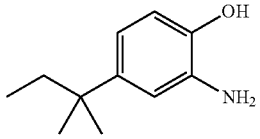 | 5% | 35% | 43% | 56% | 26% | 23% |
| 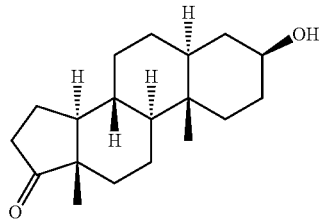 | 65% | 72% | 80% | 76% | 74% | 73% |
| 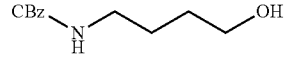 | 57% | 77% | 89% | 87% | 87% | 81% |
| 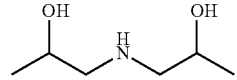 | 50% | 53% | 52% | 75% | 50% | 53% |

TABLE 105-continued

Recovery yields of model compounds using a mixture of HF/pyr/pyr after the resin
had previously been subjected to a mixture of TMG/acetic acid to cleave phenols.

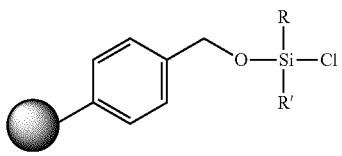

| Model Compound | R = Me<br>R' = Me | R = Et1<br>R' = Me | R = Cyclohexyl<br>R' = Methyl | R = Decyl<br>R' = Methyl | R = Isobutyl<br>R' = Methyl | R = n-Butyl<br>R' = Methyl |
|---|---|---|---|---|---|---|
| 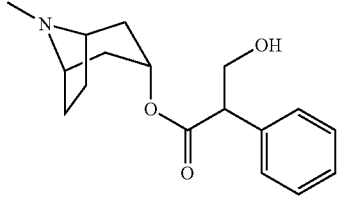 [SMILES: CN1C2CCC1CC(OC(=O)C(CO)c1ccccc1)C2] | 56% | 67% | 71% | 81% | 68% | 68% |
| 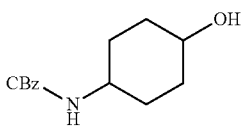 | 44% | 52% | 61% | 55% | 63% | 45% |
| 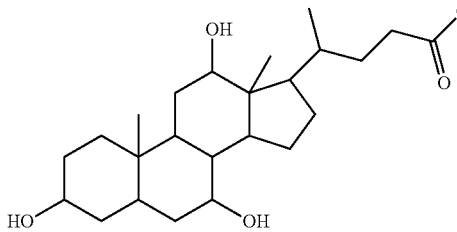 | 60% | 64% | 58% | 63% | 70% | 63% |
| 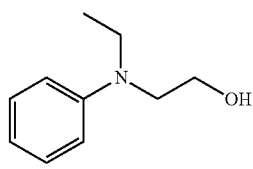 | 33% | 51% | 72% | 56% | 40% | 39% |

Preparation of *Streptomyces griseolus* Extract

*Streptomyces griseolus* (Waksman) was purchased from ATCC as a freeze-dried pellet. Cells were grown as described previously. [24] Briefly, 20 mL cultures were grown in ISP Medium 2 at 28° C. for ten days yielding white spores. Cells were pelleted by centrifugation at 2000 g for 10 min at 25° C. The broth was decanted, transferred to a separatory funnel and extracted according to the following protocol: EtOAC (2×300 mL), CHCl$_3$ (2×300 mL), hexanes (2×300 mL), diethyl ether (2×300 mL), 3:1 CHCl$_3$:MeOH (3×300 mL). All organic washes were combined and evaporated under reduced pressure yielding 171 mg of crude material. This material was dissolved in 2 mL of THF and 2 mL of MeOH. From this solution, 5 µL was analyzed on the LC-MS-TOF to quantify the amount of anisomycin present in the crude extract (223 nmol).

Enrichment of Endogenously Produced Anisomycin (108)

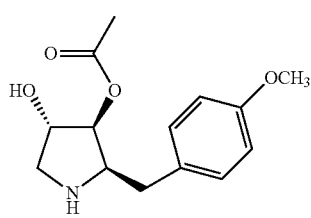

108

Bacterial extract material (29 mg) was dissolved in 3 mL of anhydrous THF and 2.4 mL of anhydrous DMSO. The chemoselective compound mixture (600 µL solution containing 223 nmol each of cortisone, trans-androsterone, N-Boc-L-Cys-OMe, tryptamine, and Fmoc-Val-OH in THF) was added and the total volume was brought to 6 mL with THF. Six 20 mL scintillation vials were charged with 400 mg ("10 equivalents"; see below) of hydroxymethyl polystyrene and activated with dichlorodiethylsilane as described. This amount of resin was chosen by estimation of the theoretical number of moles of material in the bacterial extract based on the assumption that the average compound molecular weight was 200 Da. Comparable results were obtained with fewer "equivalents" as long as an alcohol capture standard was included to ensure that resin was not the limiting reagent.

After 4 h, each vial of resin was transferred to a 10 mL biospin vessel and washed twice under Ar with 4 mL of anhydrous $CH_2Cl_2$. The resin was then transferred back to a freshly dried 20 mL scintillation vial. Five vials were immediately placed under an atmosphere of Ar and the sixth vial was rinsed with MeOH/THF to hydrolyze the activated resin, to yield an unactivated control resin. Next, to all vials was added 83 µL of freshly distilled triethylamine and 1 mL of the mixture of the crude bacteria extract containing the chemoselective set of compounds. The vials were capped and agitated overnight at room temperature. The resin was transferred to 10 mL biospin vessels and subjected to the wash protocol. The resin vessels were dried overnight in a vacuum desiccator at 30 mmHg. The dried resin was transferred to 20 mL polypropylene vial and swelled with 3 mL of anhydrous THF. To each vial was added 1 mL of a 50/50 mixture (v/v) of HF·pyridine (70/30 wt %)/pyridine (16 mmol of HF, 28 equiv relative to Si). The vials were capped and agitated for 3 h at room temperature. After this time, 5 mL of TMSOMe (36 mmol, 83 equiv relative to Si) was added to quench excess HF and the resin was agitated for an additional 30 min at room temperature. The resin was washed with THF (3×2 mL×10 min) and filtered over a 10 mL fritted polypropylene column into a 20 mL scintillation vial. The THF wash was then concentrated under reduced pressure with no heating and the sample was dissolved in 400 µL of 2:1:1 $H_2O$/THF/MeOH. Analysis was performed by injection of 5 µL of this solution onto a LC-MS-TOF and comparing the observed peak area to that of standard curve data. Comparison of the TIC of the crude bacterial extract to that of the captured molecules and the TIC obtained following extract exposure to deactivated resin is also illustrates that alcohol enrichment results only from specific interactions with the activated siloxyl-functionalized resin. LC-MS analysis demonstrates that amine-, thiol-, and carboxylic acid-containing compounds were not enriched in this experiment. Extracted ion chromatograms of alcohols captured from *Streptomyces griseolus* broth show that endogenously-produced anisomycin (108) was captured (30.5 nmol, 82% recovery) in addition to the two additional alcohols that were spiked into the extract (223 nmol each) before the capture and release (i.e., cortisone, 106, 113 nmol, 51% recovery and trans-androsterone 107, 119 nmol, 53% recovery).

While certain embodiments of the present invention have been described and/or exemplified above, it is contemplated that considerable variation and modification thereof are possible. Accordingly, the present invention is not limited to the particular embodiments described and/or exemplified herein.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

Resin Bearing More than One Functional Group Per Side Chain

In one embodiment of any of the resins described herein, a side chain may bear more than one silicon containing functional group as a reversible enrichment tag. In one embodiment, the side chain bearing more than one silicon containing functional group as a reversible enrichment tag is a disubstituted phenyl group, for example as shown in Scheme 104, which demonstrates separation of aromatic alcohols from aliphatic alcohols.

Scheme 104. Chemoselective release of aryl hydroxyl containing molecules, followed by isolation of those molecules that contain an aliphatic hydroxyl moiety.

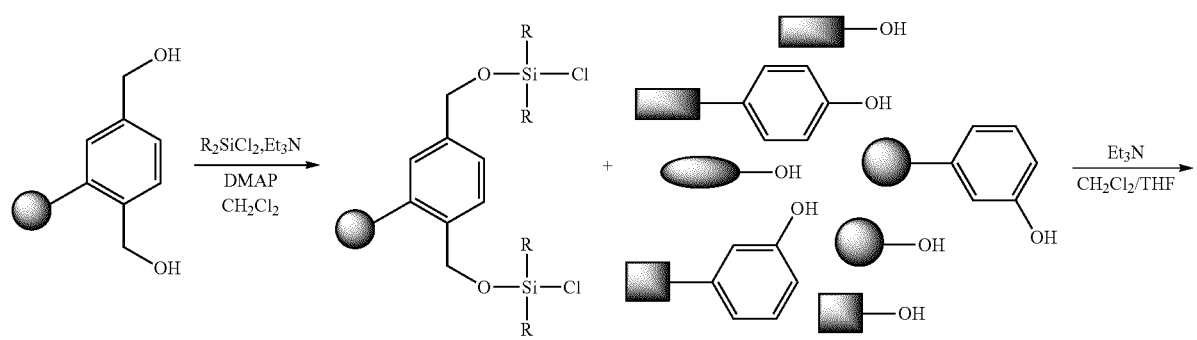

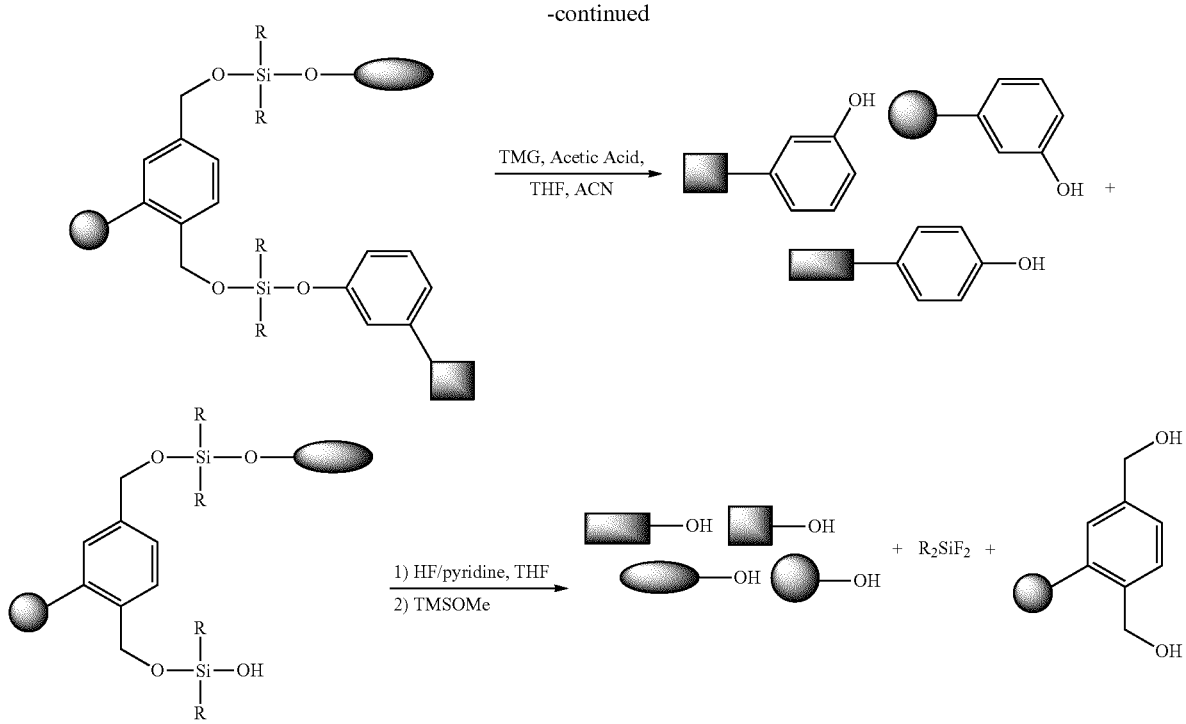

PART B—REFERENCES

1. J. Clardy and C. Walsh, Nature, 2004, 432, 829-837.
2. D. J. Newman and G. M. Cragg, J. Nat. Prod., 2007, 70, 461-477.
3. E. E. Carlson, ACS Chem. Biol., 2010, 5, 639-653.
4. T. Böttcher, M. Pitscheider and S. A. Sieber, Angew. Chem. Int. Ed., 2010, 49, 2680-2698.
5. S. D. Sarker, Z. Latif and A. I. Gray, eds., Natural products isolation, Second edn., Humana Press, Totowa, N.J., 2006.
6. F. E. Koehn and G. T. Carter, Nature Rev. Drug Discov., 2005, 4, 206-220.
7. M. S. Butler, J. Nat. Prod., 2004, 67, 2141-2153.
8. O. Sticher, Nat. Prod. Rep., 2008, 25, 517-554.
9. M. Månsson, R. K. Phipps, L. Gram, M. H. Munro, T. O. Larsen and K. F. Nielsen, J. Nat. Prod., 2010, 73, 1126-1132.
10. J. J. Araya, G. Montenegro, L. A. Mitscher and B. N. Timmerman, J. Nat. Prod., 2010, 73, 1568-1572.
11. A. Cheminat, C. Benezra, M. J. Farrall and J. M. J. Fréchet, Can. J. Chem., 1981, 59, 1405-1414.
12. J. M. J. Fréchet, A. J. Hagen, C. Benezra and A. Cheminat, Pure & Appl. Chem., 1982, 54, 2181-2188.
13. E. E. Carlson and B. F. Cravatt, Nat. Methods, 2007, 4, 429-435.
14. E. E. Carlson and B. F. Cravatt, J. Am. Chem. Soc., 2007, 129, 15780-15782.
15. M. Gualtieri, F. Baneres-Roquet, P. Villian-Guillot, M. Pugniere and J.-P. Leonetti, Curr. Med. Chem., 2009, 16, 390-393.
16. K. Grabowski, K.-H. Baringhaus and G. Schneider, Nat. Prod. Rep., 2008, 25, 892-904.
17. J. A. Tallarico, K. M. Depew, H. E. Pelish, N. J. Westwood, C. W. Lindsley, M. D. Shair, S. L. Schreiber and M. A. Foley, J. Comb. Chem., 2001, 3, 312-318.
18. Y. Hu, J. A. Porco, J. W. Labadie and O. W. Gooding, J. Org. Chem., 1998, 63, 4518-4521.
19. C. M. DiBlasi, D. E. Macks and D. S. Tan, Org. Lett., 2005, 7, 1777-1780.
20. M. M. Meloni, P. D. White, D. Armour and R. C. D. Brown, Tetrahedron, 2007, 63, 299-311.
21. T. L. Boehm and H. D. H. Showalter, J. Org. Chem., 1996, 61, 6498-6499.
22. B. A. Sobin and J. Tanner, F. W., J. Am. Chem. Soc., 1954, 76, 4053.
23. A. P. Grollman, J. Biol. Chem., 1967, 242, 3226-3233.
24. H. D. Isenberg, ed., Clinical Microbiology Procedures Handbook, American Society for Microbiology, Washington, D.C., 1992.

What is claimed is:

1. A polymeric reagent for use in the selective enrichment of hydroxyl-group-containing compounds from a mixture:
    comprising a polymer having one or more functional groups of formula $(CH_2)_n$—O—$Si(R^1)(R^2)X$ covalently attached to the polymer
    wherein
    the functional group is capable of reacting with the hydroxyl group-containing compounds when the mixture containing the compounds contacts the reagent;
    n is 1 to 4;
    $R^1$ and $R^2$ are independently selected in each instance from the group consisting of $C_1$-$C_8$ alkyl and $C_3$-$C_8$ cycloalkyl; and
    X is selected from the group consisting of Cl, Br, and $OS(O)_2CF_3$; wherein the polymer is a polyolefin, polyamide, polyurethane, or polycarbonate.

2. A polymeric reagent for use in the selective enrichment of hydroxyl-group-containing compounds from a mixture:
    comprising a polymer having one or more functional groups of formula $(CH_2)_n$—O—$Si(R^1)(R^2)X$ covalently attached to the polymer wherein
the functional group is capable of reacting with the hydroxyl group-containing compounds when the mixture containing the compounds contacts the reagent;
n is 1 to 4;
$R^1$ and $R^2$ are independently selected in each instance from the group consisting of $C_1$-$C_8$ alkyl and $C_3$-$C_8$ cycloalkyl; and
X is selected from the group consisting of Cl, Br, and $OS(O)_2CF_3$; wherein the polymeric reagent is a polystyrene of formula

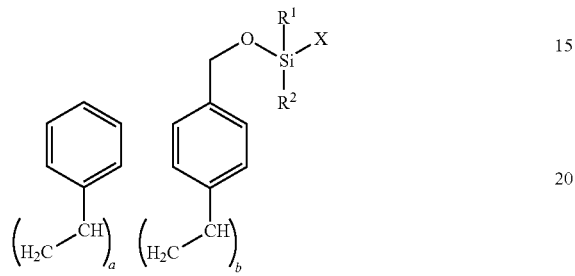

wherein the ratio of b to a is from 1:99 to 1:1, and wherein the polystyrene is crosslinked with from 0.5 to 10.0% divinylbenzene.

* * * * *